(12) United States Patent
Mallampalli et al.

(10) Patent No.: US 8,187,821 B2
(45) Date of Patent: May 29, 2012

(54) COMPOSITIONS AND METHODS FOR THE MODULATION OF PGRMC1

(75) Inventors: Monica Mallampalli, Ellicott City, MD (US); James Metherall, Salt Lake City, UT (US); Darren Warnick, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 373 days.

(21) Appl. No.: 12/436,316

(22) Filed: May 6, 2009

(65) Prior Publication Data

US 2009/0280515 A1    Nov. 12, 2009

Related U.S. Application Data

(60) Provisional application No. 61/127,096, filed on May 8, 2008.

(51) Int. Cl.
   *G01N 33/53* (2006.01)
(52) U.S. Cl. ......................................... 435/7.2
(58) Field of Classification Search .................. None
   See application file for complete search history.

(56) References Cited

U.S. PATENT DOCUMENTS 6,236,946 B1 *  5/2001  Scanlan et al. .................. 702/22

OTHER PUBLICATIONS

Content et al., "Expression and preliminary deletion analysis of the 42 kDa 2-5A synthetase induced by human interferon," in Biological Interferon Systems, Proceedings of ISIR-TNO Meeting on Interferon Systems, Cantell (ed.), pp. 65-72, Nijhoff 1987.

Coumailleau et al., "Definition of a Minimal Domain of the Dioxin Receptor that is Associated with Hsp90 and Maintains Wild Type Ligand Binding Affinity and Specificity," *J. Biol. Chem.*, 270: 25291-25300, 1995.

Cunningham, Brian C. and James A. Wells, "High-Resolution Epitope Mapping of hGH-Receptor Interactions by Alanine-Scanning Mutagenesis," *Science*, 244:1081-1085, 1989.

Fukunaga et al., "Identification of Functional Domains of the Aryl Hydrocarbon Receptor," *J. Biol. Chem.*, 270: 29270-29278, 1995.

Herschman, "The EGF Receptor," in Control of Animal Cell Proliferation, vol. 1, Boynton et al., (eds.) pp. 169-199, Academic Press 1985.

Meisel, Lee and Eric Lam, "The conserved ELK-homeodomain of KNOTTED-1 contains two regions that signal nuclear localization," *Plant Molec. Biol.*, 30:1-14, 1996.

Treuter et al., "Promoter specificity and deletion analysis of three heat stress transcription factors of tomato," *Molec. Gen. Genet.*, 240:113-125, 1993.

Yamaguchi, Yumi and M. Tien Kuo, "Functional Analysis of Aryl Hydrocarbon Receptor Nuclear Translocator Interactions with Aryl Hydrocarbon Receptor in the Yeast Two-Hybrid System," *Biochem. Pharmacol.*, 50:1295-1302, 1995.

\* cited by examiner

*Primary Examiner* — Michael Pak
(74) *Attorney, Agent, or Firm* — Joseph P. Meara; Foley & Lardner LLP

(57) ABSTRACT

The present invention provides for novel assays and the use of such assays for screening compounds that affect PGRMC1's and related homologue's ability to catalyze the incorporation of cholesterol into membranes. The present invention also provides for methods and compositions for affecting incorporation of cholesterol into membranes. The invention also provides for diagnostic and therapeutic kits for the methods described herein.

17 Claims, 10 Drawing Sheets

COMPOSITIONS AND METHODS FOR THE MODULATION OF PGRMC1

CROSS-REFERENCE TO RELATED APPLICATIONS

This application claims priority to U.S. Provisional Patent Application No. 61/127,096, filed May 8, 2008, the entire contents of which are hereby incorporated by reference in its entirety.

TECHNICAL FIELD

The present technology relates generally to the fields of molecular biology and pharmacology and to the diagnosis, prognosis, or prevention/therapeutic treatment of disease characterized by defects in cellular cholesterol homeostasis. In particular, the technology relates to screening methods for identifying compounds that affect the ability of PGRMC1 or a homologue thereof to catalyze the incorporation of cholesterol into membranes.

BACKGROUND

The following description is provided to assist the understanding of the reader. None of the information provided or references cited are admitted to be prior art to the present invention.

Cholesterol is a lipid that plays a key role in the biology of mammalian cells. It helps to build and maintain the integrity of cell membranes, serves as a precursor for the synthesis of vitamin D and of the various steroid hormones, plays a role in cell signaling processes, and aids in the manufacture of bile and in the metabolism of fat soluble vitamins. Because cholesterol is insoluble in water, the body makes lipoproteins to help the extracellular transport of cholesterol in the circulatory system. Low-density lipoproteins ("LDL") carry cholesterol from the liver to body tissues which need it. High density lipoproteins ("HDL") pick up cholesterol in the blood stream and carry it back to the liver where it is converted into bile and used for digestion. Cholesterol being carried to the body tissues by low-density lipoproteins is taken up by cells via LDL receptor-mediated endocytosis so that it can be used in its various capacities.

A complex set of homeostatic mechanisms maintains strict control over the level of cholesterol within the cell. Although it is known that intracellular cholesterol levels are regulated through a complex set of transcriptional and post-transcriptional feedback mechanisms, intracellular sterol transport is generally a poorly understood cellular process. It is known, however, that the endoplasmic reticulum is the site of the late steps of cholesterol biosynthesis and of all of the cholesterol homeostatic mechanisms including activation of transcriptional regulation of sterol-regulated genes through SREBP, the regulated degradation of HMG-CoA-reductase, and storage of excess cholesterol in the form of cholesteryl esters. Consequently, the specific delivery of sterols to the endoplasmic reticulum is required for cholesterol biosynthesis and normal cholesterol homeostasis.

Defects in the mechanisms of cellular cholesterol homeostasis can lead to developmental and/or neurodegenerative disorders as well increased levels of circulating LDL and an increased risk of coronary heart disease. Coronary heart disease is caused by atherosclerosis, or a buildup of plaque, in the walls of the coronary arteries. Plaque is composed of cholesterol and other fatty materials. As the deposits slowly narrow the coronary arteries, the heart receives less blood. Eventually, diminished blood flow may cause angina pectoris or myocardial infarction. Angina pectoris is chest pain or discomfort that occurs when an insufficient amount of enough oxygen-rich blood is flowing to an area of the heart muscle. This causes pressure and pain in the chest, shoulders, arms, neck, back, and jaw. Myocardial infarction, commonly known as a heart attack, occurs when blood flow to an area of the heart muscle is completely blocked. This prevents oxygen-rich blood from reaching that area of the heart muscle, subsequently causing it to die. Without immediate treatment, myocardial infarction can lead to serious problems and even death.

Because improper regulation of cholesterol homeostasis can lead to serious health problems, there remains a need for a better understanding of the intracellular cholesterol transport mechanisms which will allow for more appropriate and accurate diagnosis and treatment.

SUMMARY

In one aspect, the invention provides a method of screening for compounds that modulate the activity of PGRMC1 or a homologue thereof comprising: (a) contacting a test compound with cholesterol and a membrane-bound PGRMC1 or a homologue thereof to form a reaction mixture; and (b) determining whether incorporation of cholesterol into the membrane is increased or decreased in the presence of the test compound, wherein a decrease in the incorporation is an indication that the test compound inhibits the activity of PGRMC1 or homologue thereof, and an increase in the incorporation is an indication that the test compound enhances the activity of PGRMC1. The method of screening may be used to identify compounds that inhibit incorporation of cholesterol into a membrane. The method of screening may also be used to identify compounds that can be used to treat diseases characterized by defects in cholesterol homeostasis. For example, the disease characterized by defects in cholesterol homeostasis may be hypercholesterolemia, cardiovascular disease (such as atherosclerosis), neurodegenerative disease, or developmental disorders.

In one embodiment, the PGRMC1 or homologue thereof is SEQ ID NO: 1 or a protein having an amino acid sequence that is at least 95% identical to SEQ ID NO: 1. In a particular embodiment, the PGRMC1 or homologue thereof is SEQ ID NO: 1.

In an illustrative embodiment, the step of determining whether incorporation of cholesterol into the membrane is increased or decreased in the presence of the test compound comprises: (a) contacting the reaction mixture with cholesterol oxidase; (b) adding peroxidase and a detection reagent; and (c) measuring the formation of a detectable product. For example, the detectable product may be a colored, luminescent or fluorescent product. In a suitable embodiment, the detection reagent is 3,3'-diaminobenzidine tetrahydrochloride.

In one embodiment, the membrane-bound PGRMC1 protein or homologue thereof is produced recombinantly. For example, the membrane-bound PGRMC1 protein or homologue thereof may be produced in *E. coli*.

In one embodiment, the test compound is contacted with cholesterol and a membrane-bound PGRMC1 or a homologue thereof under physiological conditions.

In one embodiment, the invention provides a method of screening compounds that modulate the activity of PGRMC1 or a homologue thereof comprising: (a) providing a solution comprising (i) membranes associated with PGRMC1 or a homologue thereof, (ii) cholesterol; and (iii) a test compound;

(b) incubating the solution under physiological conditions; (c) contacting the solution with cholesterol oxidase; (d) adding peroxidase and a detection reagent to produce a detectable product; and (e) measuring the production of the detectable product to determine whether incorporation of cholesterol into the membrane is increased or decreased in the presence of the test compound.

In another aspect, the invention provides for methods and compositions for affecting the ability of PGRCM1 or a homologue thereof to catalyze the incorporation of cholesterol into cell membranes. The invention also provides for diagnostic and therapeutic kits for the methods described herein.

BRIEF DESCRIPTION OF THE DRAWINGS

The following figures illustrate particular embodiments of the present invention.

DETAILED DESCRIPTION

Figure 1:
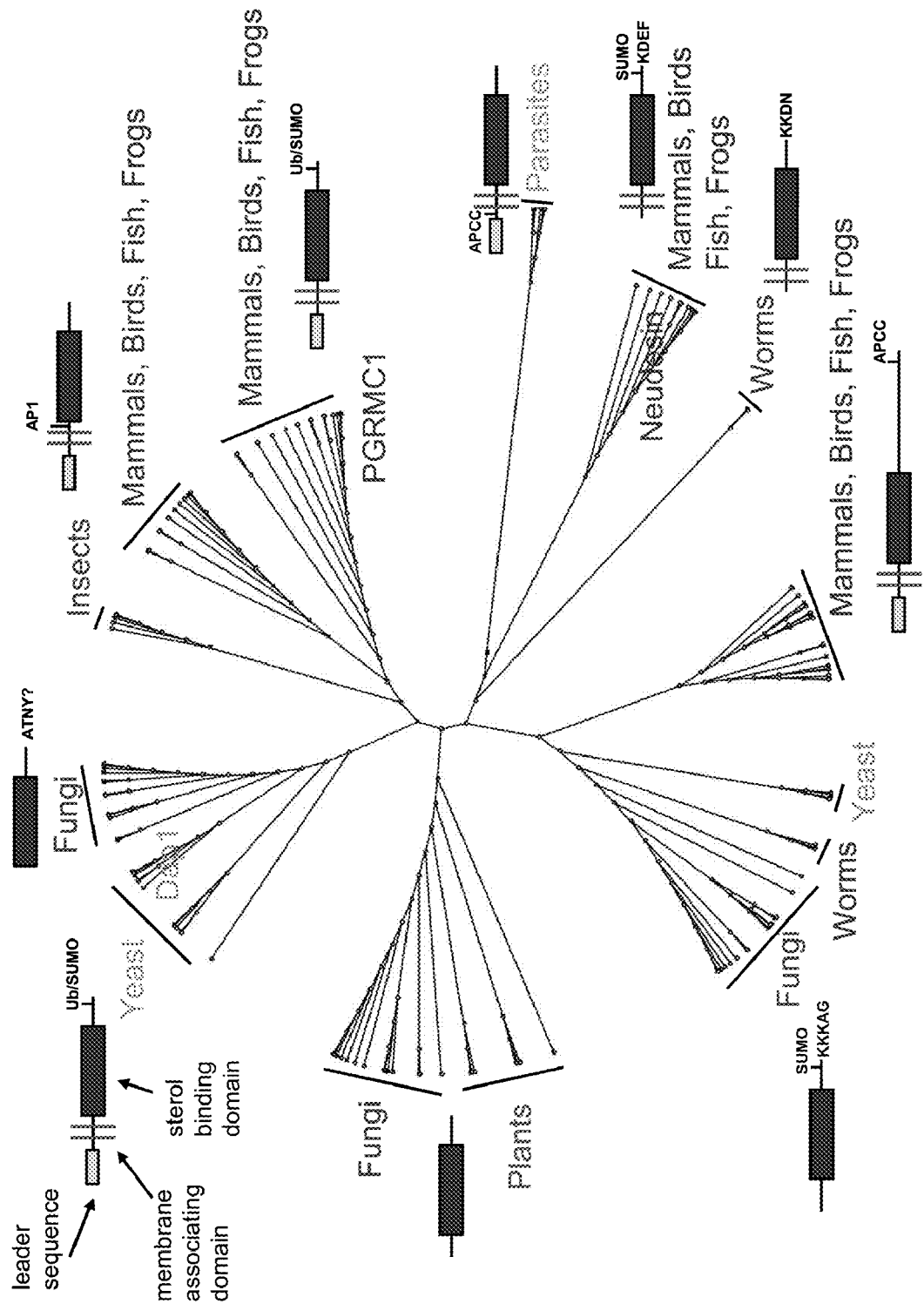
FIG. 1 illustrates the relationship between progesterone receptor membrane component 1 ("PGRMC1") and related proteins throughout eukaryotes. 'ATNY,' 'KKKAG,' 'KKDN,' and 'KDEF' disclosed as SEQ ID NOS 10-13 respectively.

One of the most common methods of treating disorders of cholesterol homeostasis is administration of statins, a class of drugs that lower cholesterol levels in people with or at risk of cardiovascular disease. Statins lower cholesterol by inhibiting the enzyme HMG-CoA reductase, which is the rate-limiting enzyme of the mevalonate pathway of cholesterol synthesis. Inhibition of this enzyme in the liver results in decreased cholesterol synthesis as well as increased synthesis of LDL receptors, resulting in an increased clearance of low-density lipoprotein (LDL) from the bloodstream. However, statins also block the production of important metabolites such as ubiquinone, dolichol, and isoprenoids, for which cholesterol is a precursor. The inability to synthesize these compounds likely causes some of the common side effects seen in statin-treated individuals.

In one aspect, the screening methods of the present invention seek to identify compounds that advantageously lack the side effects caused by statins. The methods of the present invention relate to the modulation of cholesterol delivery to intracellular membranes, such as the multivesicular body and the endoplasmic reticulum. Such methods may provide a basis for therapeutic approaches that do not have the unintended consequences of inhibiting the generation of metabolites which require cholesterol as a precursor. Such treatments might also be combined with currently available statin therapies, to allow a reduction in dosage that would help relieve some of the side effects associated with current treatments.

DEFINITIONS

The present technology is described herein using several definitions, as set forth throughout the specification. As used herein, unless otherwise stated, the singular forms "a," "an," and "the" include the plural reference. Thus, for example, a reference to "a protein" is a reference to one or more proteins.

As used herein, the term "diagnosis" means detecting a disease or disorder or determining the stage or degree of a disease or disorder. The term "diagnosis" also encompasses determining the therapeutic effect of a drug therapy, or predicting the pattern of response to a drug therapy. The diagnostic methods may be used independently, or in combination with other diagnosing and/or staging methods known in the medical art for a particular disease or disorder, e.g., a disease characterized by defects in cellular cholesterol homeostasis.

As used herein, the term "disease characterized by defects in cellular cholesterol homeostasis" include any disease or medical condition associated with a defect in cholesterol metabolism. Examples of diseases characterized by defects in cellular cholesterol homeostasis include, but are not limited to, hypercholesterolemia, atherosclerosis, coronary heart disease, and neurodegenerative disease.

As used herein, the term "effective amount" of a test compound is a quantity sufficient to achieve a desired therapeutic and/or prophylactic effect, for example, an amount which results in the prevention of or a decrease in the symptoms associated with a disease that is being treated, i.e., a disease characterized by defects in cellular cholesterol homeostasis. The amount of compound administered to the subject will depend on the type and severity of the disease and on the characteristics of the individual, such as general health, age, sex, body weight and tolerance to drugs. It will also depend on the degree, severity or stage of disease. The skilled artisan will be able to determine appropriate dosages depending on these and other factors.

As used herein, the term "ESCRT1" refers to endosomal sorting complex required for transport 1.

As used herein, the term "endoplasmic reticulum" refers to an organelle found in all eukaryotic cells that is an interconnected network of tubules, vesicles and cisternae. The endoplasmic reticulum is responsible for several specialized functions including protein translation, folding and transport of proteins to be used in the cell membrane or to be secreted from the cell, sequestration of calcium; and production and storage of glycogen, steroids, and other macromolecules.

As used herein, the term "PGRMC1 homologue" refers to a member of a family of proteins that share homology (i.e., sequence identity) with PGRMC1, including PGRMC2 and neudesin, and catalyzes the incorporation of sterols, including cholesterol, into membranes. In some embodiments, the term "homologue" refers to the relationship between proteins that have a common evolutionary origin and differ because they originate from different species. For example, human PGRMC1 is a homologue of mouse PGRMC1. The term homologue also includes mutants and variants of a naturally occurring polypeptide sequence.

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection (See, e.g., NCBI web site). Such sequences are then said to be "substantially identical." This term also refers to, or can be applied to, the complement of a test sequence. The term also includes sequences that have deletions and/or additions, as well as those that have substitutions. Typically, identity exists over a region that is at least about 25 amino acids or nucleotides in length, or more preferably over a region that is at least 50-100 amino acids or nucleotides in length.

As used herein, the term "ligand" refers to substance that is able to bind to and form a transient or stable complex with a biomolecule to serve a biological purpose, for example a substrate which interacts with an enzyme in the process of an enzymatic reaction. Ligands also include signal triggering molecules which bind to sites on a target protein, by intermolecular forces such as ionic bonds, hydrogen bonds and Van der Waals forces.

As used herein, the term "modulation" refers to a change in the level or magnitude of an activity or process. The change may be either an increase or decrease compared to a control or reference sample.

As used herein, the term "multivesicular body" or "MVB" is a type of late endosome in which regions of the limiting endosomal membrane invaginate to form internal vesicles. The multivesicular body (MVB) pathway is responsible for both the biosynthetic delivery of lysosomal hydrolases and the downregulation of numerous activated cell surface receptors which are degraded in the lysosome. For the purposes of the present invention, "lysosome" refers to organelles that contain digestive enzymes, or acid hydrolases, that digest organelles, food particles, and engulfed viruses or bacteria. For the purposes of the present invention, "endosome" refers to a membrane-bound compartment inside a cell.

As used herein, the term "NPC1" refers to the protein encoded by the NPC1 (Neimann-Pick disease, type C1) gene. This protein is located mainly in the membranes of the lysosomes and endosomes. This protein plays a role in the movement of cholesterol and other types of lipids across cell membranes.

As used herein, the term "PGRMC1" refers to a protein encoded by the PGRMC1 (Progesterone receptor membrane component 1) gene. This protein is a putative steroid membrane receptor expressed predominantly in the liver and kidney.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the term "progesterone" refers to a steroid hormone involved in the female menstrual cycle, pregnancy, and embryogenesis of humans and other species. Males produce progesterone as well, but in a lower amount than produced by women.

As used herein, the term "sample" may include, but is not limited to, bodily tissue or a bodily fluid such as blood (or a fraction of blood such as plasma or serum), lymph, mucus, tears, saliva, sputum, urine, semen, stool, CSF, ascities fluid, or whole blood, and including biopsy samples of body tissue. A sample may also include an in vitro culture of microorganisms grown from a sample from a subject. A sample may be obtained from any subject, e.g., a subject/patient having or suspected to have a disease or condition characterized by defects in cellular cholesterol homeostasis.

As used herein, the term "screening" means determining whether a test compound has capabilities or characteristics of preventing or slowing down (lessening) the targeted pathologic condition stated herein, namely a disease or condition characterized by defects in cellular cholesterol homeostasis.

As used herein, the term "sterol" refers to subgroup of steroids with a hydroxyl group in the 3-position of the A-ring. Sterols play essential roles in the physiology of eukaryotic organisms. For example, cholesterol forms part of the cellular membrane where its presence affects the cell membrane's fluidity and serves as a secondary messenger in developmental signaling.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who is, or is suspected to be, afflicted with a disease or condition characterized by defects in cellular cholesterol homeostasis.

As used herein, the term "ubiquitination" refers to the attachment of the protein ubiquitin to lysine residues of other molecules. Ubiquination of a molecule, such as a peptide or protein, can act as a signal for its rapid cellular degradation, and for targeting to the MVB via interaction with ESCRT1 proteins.

As used herein, the terms "variant" or "mutant" are used to refer to a protein or peptide which differs from a naturally occurring protein or peptide (i.e., the "prototype" or "wild-type" protein) by modifications to the naturally occurring protein or peptide, but which maintains the basic protein and side chain structure of the naturally occurring form. Such changes include, but are not limited to: changes in one, few, or even several amino acid side chains; changes in one, few or several amino acids, including deletions (e.g., a truncated version of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A "variant" or "mutant" can have either enhanced, decreased, changed, or substantially similar properties as compared to the naturally occurring protein or peptide. In one embodiment, a variant of PGRMC1 catalyzes the incorporation of those sterols, including cholesterol into specific membranes.

Overview

The present invention provides for PGMRC1 and its homologues as novel diagnostic and therapeutic targets for disease characterized by defects in cellular cholesterol homeostasis. The human protein PGRMC1 and its homologues have been previously characterized by a number of independent groups in different systems and are involved in a wide variety of biological processes. A wide variety of ligands have also been proposed to interact with PGRMC1. The initial characterization studies have suggested that the protein binds to progesterone. Structurally, PGRMC1 has a putative ligand binding domain very similar to the cytochrome $b_5$ heme binding domain (See, e.g., amino acids 72-170 of SEQ ID NO: 1); however, PGRMC1 lacks two iron-chelating histidine residues that are absolutely conserved in cytochrome $b_5$ proteins.

The inventors believe they have identified a ligand and function for PGRMC1 that has not been previously described. It was discovered that PGRMC1 exhibited a six-fold higher level of expression in NPC1 mutant fibroblasts versus wild-type fibroblasts when they performed a gene expression microarray analysis to determine the effects that mutant NPC1 has on global gene expression. Loss of function mutations in NPC1 result in defects in the transport of LDL-derived cholesterol from the endosome to lysosomes and to the plasma membrane.

Unexpectedly, it was discovered that progesterone is likely not the natural ligand for PGRMC1. Results demonstrated that while PGRMC1 can bind progesterone, it binds cholesterol with higher affinity and likely functions by catalytically delivering its bound cholesterol to cellular membranes. The inventors also found that human PGRMC1 is mono-ubiquitinated. Mono-ubiquitinated proteins are known to be recognized by ESCRT1 and targeted to the MVB pathway. While not wishing to be limited by theory, these observations strongly suggest that PGRMC1 is targeted to the MVB. Cholesterol is required for aspects of MVB formation and function. Specifically enriching the MVB membranes with cholesterol would be difficult to do using vesicular delivery since the vesicles would also include large quantities of fatty acids and other membrane components. PGRMC1, by specifically transporting cholesterol into the membranes, would allow the composition of the membranes to change as compared to the membranes that are delivered to the MVB.

While not wishing to be limited by theory, PGRMC1 may actively transfer sterols to the MVB membrane through some sort of conformational change or it may simply act by increasing the local concentration of cholesterol near the membrane allowing it to enter the membrane through passive diffusion. It appears that the process does not require energy since cholesterol was transferred efficiently using washed membranes in the absence of ATP. Regardless, either mechanism would result in catalyzing the delivery of sterols to the associated membrane.

There are four proteins (PGRMC1, PGRMC2, neudesin, and a fourth uncharacterized protein) that share homology with PGRMC1. Each protein is a member of a related family with homologues in other mammals, birds, fish, frogs, and other eukaryotes. (FIG. 1) In addition to these four families, there are homologous proteins conserved in plants, fungi, parasites, worms, and insects. All of these proteins appear to share the heme/steroid binding domain but lack the conserved histidine residues required for chelating the iron in cytochrome-$b_5$ proteins. Careful analyses of the different motifs conserved in each family suggest that the entire family of related proteins binds sterols, and catalyzes the incorporation of those sterols into specific membranes. Different gene products may transport sterols into different subcellular compartments, with specific motifs within each protein serving to target that protein to a specific membrane where sterol incorporation occurs. Therefore, the entire family of proteins may bind sterols, whether it is cholesterol in humans, ergosterol in yeast, or phytosterols in plants.

The present invention provides for PGRMC1 and its homologues as novel diagnostic and therapeutic targets for disease characterized by defects in cellular sterol and cholesterol homeostasis. In one aspect, the invention provides for assays and the use of such assays for screening compounds that affect the ability of PGRMC1 and its homologues to catalyze the incorporation of cholesterol into membranes. In another aspect, the invention provides for methods and compositions for affecting PGRMC1's or a homologue's ability to catalyze the incorporation of cholesterol or other sterols into cell membranes. The invention also provides for diagnostic and therapeutic kits for the methods described herein. This may provide a useful target for the diagnosis and treatment of developmental and/or neurodegenerative disorders as well increased levels of circulating LDL and an increased risk of coronary heart disease.

PGMRC1 Proteins and Homologues

As used herein, reference to an isolated protein or polypeptide, including an isolated PGMRC1, includes full-length proteins, fusion proteins, or any fragment, mutant, variant, or homologue of such a protein. Such a PGMRC1 protein can include, but is not limited to, purified PGMRC1 protein, recombinantly produced PGMRC1 protein, soluble PGMRC1 protein, insoluble PGMRC1 protein, and isolated PGMRC1 protein associated with other proteins, and isolated PGMRC1 associated with cellular membranes. More specifically, an isolated protein is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Typically, an isolated PGMRC1 protein is produced recombinantly.

In addition, and by way of example, a "human PGMRC1 protein" refers to a PGMRC1 protein from a human (*Homo sapiens*) or to a PGMRC1 protein that has been otherwise produced from the knowledge of the structure (e.g., sequence) and perhaps the function of a naturally occurring PGMRC1 protein from *Homo sapiens*. In other words, a human PGMRC1 protein includes any PGMRC1 protein that has substantially similar structure and function of a naturally occurring PGMRC1 protein from *Homo sapiens* or that is a biologically active (i.e., has biological activity) homologue of a naturally occurring PGMRC1 protein from *Homo sapiens* as described in detail herein. As such, a human PGMRC1 protein can include purified, partially purified, recombinant, mutated/modified and synthetic proteins. According to the present invention, the terms "modification" and "mutation" can be used interchangeably, particularly with regard to the modifications/mutations to the amino acid sequence of PGMRC1 (or nucleic acid sequences) described herein. The amino acid sequence of human PGMRC1 (Genbank Accession No. NP_006658) is set forth below as SEQ ID NO: 1.

```
                                                  (SEQ ID NO: 1)
MAAEDVVATGADPSDLESGGLLHEIFTSPLNLLLLGLCIFLLYKIV

RGDQPAASGDSDDDEPPPLPRLKRRDFTPAELRRFDGVQDPRILMA

INGKVFDVTKGRKFYGPEGPYGVFAGRDASRGLATFCLDKEALKDE

YDDLSDLTAAQQETLSDWESQFTFKYHHVGKLLKEGEEPTVYSDEE

EPKDESARKND
```

A "mouse PGMRC1 protein" refers to a PGMRC1 protein from a mouse (*Mus musculus*) or to a PGMRC1 protein that has been otherwise produced from the knowledge of the structure (e.g., sequence) and perhaps the function of a naturally occurring PGMRC1 protein from *Mus musculus*. The amino acid sequence of the *Mus musculus* PGMRC1 (Genbank Accession No. NP_058063) is set forth below as SEQ ID NO: 2. The mouse sequence is 95% identical to the human PGMRC1.

```
                                                  (SEQ ID NO: 2)
MAAEDVVATGADPSELEGGGLLHEIFTSPLNLLLLGLCIFLLYKIV

RGDQPGASGDNDDDEPPPLPRLKRRDFTPAELRRFDGVQDPRILMA

INGKVFDVTKGRKFYGPEGPYGVFAGRDASRGLATFCLDKEALKDE

YDDLSDLTPAQQETLSDWDSQFTFKYHHVGKLLKEGEEPTVYSDDE

EPKDETARKNE
```

A "rat PGMRC1 protein" refers to a PGMRC1 protein from a rat (*Rattus norvegicus*) or to a PGMRC1 protein that has been otherwise produced from the knowledge of the structure (e.g., sequence) and perhaps the function of a naturally occurring PGMRC1 protein from *Rattus norvegicus* s. The amino acid sequence of the *Rattus norvegicus* PGMRC1 (Genbank Accession No. NP_068534) is set forth below as SEQ ID NO: 3. The rat sequence is 91% identical to the human PGMRC1.

```
                                                  (SEQ ID NO: 3)
MAAEDVVATGADPSELEGGGLLQEIFTSPLNLLLLGLCIFLLYKIV

RGDQPGASGDNDDDEPPPLPRLKPRDFTPAELRRYDGVQDPRILMA

INGKVFDVTKGRKFYGPEGPYGVFAGRDASRGLATFCLDKEALKDE
```

-continued

```
YDDLSDLTPAQQETLNDWDSQFSSPSSTITWGKLLEGAEEPIVYSD

DEEQKMRLLGRVTEAVSGAYLFLYFAKSFVTFQSVFTTW
```

PGRMC1 homologues includes members of a family of proteins that share homology with PGRMC1, including PGRMC2 and neudesin. The sequence of human PGRMC2 and neudesin are set forth below as SEQ ID NOs: 4 and 5, respectively.

```
                                                  (SEQ ID NO: 4)
MAAGDGDVKLGTLGSGSESSNDGGSESPGDAGAAAEGGGWAAAALA

LLTGGGEMLLNVALVALVLLGAYRLWVRWGRRGLGAGAGAGEESPA

TSLPRMKKRDFSLEQLRQYDGSRNPRILLAVNGKVFDVTKGSKFYG

PAGPYGIFAGRDASRGLATFCLDKDALRDEYDDLSDLNAVQMESVR

EWENQFKEKYDYVGRLLKPGEEPSEYTDEEDTKDHNKQD (SEQ ID NO: 5)
MVGPAPRRRLRPLAALALVLALAPGLPTARAGQTPRPAERGPPVRL

FTEEELARYGGEEEDQPIYLAVKGVVFDVTSGKEFYGRGAPYNALT

GKDSTRGVAKMSLDPADLTHDTTGLTAKELEALDEVFTKVYKAKYP

IVGYTARRILNEDGSPNLDFKPEDQPHFDIKDEF
```

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in PGMRC1 homologues, as compared to the wild-type protein, either increase, decrease, otherwise change, or do not substantially change, the basic enzymatic activity of the PGMRC1 homologue as compared to the naturally occurring protein. Some modifications in PGMRC1 homologues increase, decrease, otherwise change, or do not substantially change, other biological activities or properties of the CBS protein as compared to the naturally occurring protein (e.g., steol binding, incorporation of sterols into lipid bilayers, etc.). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue, may result in proteins having the same biological activity as the naturally occurring protein, or in proteins having decreased, increased, or different biological activity as compared to the naturally occurring protein. Modifications which result in a decrease in protein expression or a decrease in the activity of the protein, can be referred to as inhibition (complete or partial), down-regulation, or decreased action of a protein. Similarly, modifications which result in an increase in the activity of the protein, can be referred to as amplification, overproduction, activation, enhancement, up-regulation or increased action of a protein.

Homologues or variants of PGRMC1 can be produced that contain one or more conservative or non-conservative amino acid changes, compared with the native enzyme, so long as the sterol binding or cholesterol incorporation activity is retained. Typically, variants have at least 50%, at least 60%, at least 70%, at least 80%, or at least 90% amino acid sequence identity compared to the original sequences such as any one of SEQ ID NOs: 1, 2, 3, 4, or 5. In some embodiments, high sequence identity variants are provided in which the amino acid sequence identity of the variant to the PGRMC1 is at least 95%, at least 96%, at least 97%, at least 98% or even at least 99%. In other embodiments, PGRMC1 variants include 1, 2, 3, 4, 5, 6, 7, 8, 9, 10, or more conservative or nonconservative amino acid substitutions such as 15, 20, 25, 30, or even 40 amino acid substitutions so long as cholesterol incorporation activity is retained. The ability of variants of PGRMC1 to convert insert cholesterol into lipid bilayers can be determined using a standard activity assay, such as the assay described in the Examples.

Conservative variants can be obtained that contain one or more amino acid substitutions of, e.g., SEQ ID NO: 1, in which an alkyl amino acid is substituted for an alkyl amino acid in the PGRMC1 amino acid sequence, an aromatic amino acid is substituted for an aromatic amino acid in PGRMC1 amino acid sequence, a sulfur-containing amino acid is substituted for a sulfur-containing amino acid in the PGRMC1 amino acid sequence, a hydroxy-containing amino acid is substituted for a hydroxy-containing amino acid in the PGRMC1 amino acid sequence, an acidic amino acid is substituted for an acidic amino acid in the PGRMC1 amino acid sequence, a basic amino acid is substituted for a basic amino acid in the PGRMC1 amino acid sequence, or a dibasic monocarboxylic amino acid is substituted for a dibasic monocarboxylic amino acid in the PGRMC1 amino acid sequence.

Among the common amino acids, for example, a "conservative amino acid substitution" is illustrated by a substitution among amino acids within each of the following groups: (1) glycine, alanine, (2) valine, leucine, and isoleucine, (3) phenylalanine, tyrosine, and tryptophan, (4) cysteine and methionine, (5) serine and threonine, (6) aspartate and glutamate, (7) glutamine and asparagine, and (8) lysine, arginine and histidine.

Conservative amino acid changes in e.g., the human PGRMC1, can be introduced by substituting appropriate nucleotides for the nucleotides encoding SEQ ID NO: 1. Such "conservative amino acid" variants can be obtained, for example, by oligonucleotide-directed mutagenesis, linker-scanning mutagenesis, mutagenesis using the polymerase chain reaction, and the like. Ausubel et al., supra; Ausubel et al. (eds.), SHORT PROTOCOLS IN MOLECULAR BIOLOGY, 5th Edition, John Wiley & Sons, Inc. (2002). Also see generally, McPherson (ed.), DIRECTED MUTAGENESIS: A PRACTICAL APPROACH, IRL Press (1991). A useful method for identification of locations for sequence variation is called "alanine scanning mutagenesis" a described by Cunningham and Wells in Science, 244:1081-1085 (1989).

PGRMC1 variants that contain one or more non-conservative amino acid substitutions, such as those based on PGRMC1 having any one of SEQ ID NOs: 1, 2, and 3 and that retain the ability to incorporate cholesterol into lipid bilayers can also be produced and used as disclosed herein. Non-conservative amino acid substitutions are known in the art and include, without limitation, leucine for aspartate or valine for threonine. Non-conservative variants can also include amino acid insertions as compared to the native sequence such as, without limitation, insertion of methionine. As will be appreciated by the skilled artisan, the same methods used for generating conservative variants may be adapted and used to produce nonconservative variants.

In addition, routine deletion analyses of DNA molecules can be performed to obtain "functional fragments" of PGRMC1 or other homologues. The fragments are inserted into expression vectors in proper reading frame, and the expressed polypeptides are isolated and tested for the ability to incorporate cholesterol into lipid bilayers. One alternative to exonuclease digestion is to use oligonucleotide-directed mutagenesis to introduce deletions or stop codons to specify production of a desired fragment. Alternatively, particular fragments of the PGRMC1 gene can be synthesized using the polymerase chain reaction. Standard techniques for functional analysis of proteins are described by, for example, Treuter et al., *Molec. Gen. Genet.*, 240:113 (1993); Content et al., "Expression and preliminary deletion analysis of the 42 kDa 2-5 A synthetase induced by human interferon," in BIOLOGICAL INTERFERON SYSTEMS, PROCEEDINGS OF ISIR-TNO MEETING ON INTERFERON SYSTEMS, Cantell (ed.), pages 65-72 (Nijhoff 1987); Herschman, "The EGF Receptor," in CONTROL OF ANIMAL CELL PROLIFERATION, Vol. 1, Boynton et al., (eds.) pages 169-199 (Academic Press 1985); Coumailleau et al, *J. Biol. Chem.*, 270:29270 (1995); Fukunaga et al., *J. Biol. Chem.*, 270:25291 (1995); Yamaguchi et al., *Biochem. Pharmacol.*, 50:1295 (1995); and Meisel et al., *Plant Molec. Biol.*, 30:1 (1996). In some embodiments the functional fragment retains at least 50% or at least 60% of the amino acids of the native sequence. In others the functional fragment retains at least 70%, at least 80%, at least 90%, at least 95%, at least 98% or at least 99% of the amino acids of the native sequence.

Methods of Screening for Compounds that Modulate Sterol Transfer into Membranes

In one aspect, the invention provides for methods of screening for compounds which modulate the activity of PGRMC1 or a homologue thereof. In one embodiment, a cholesterol incorporation assay is used to determine the amount of cholesterol incorporated into a membrane by PGRMC1 or a homologue using the following materials: purified membranes containing PGRMC1 or a homologue and labeled cholesterol, for example cholesterol labeled by a radioisotope, a fluorescent tag, or other detectable label. Cholesterol incorporation into the membrane is determined by isolation and washing of membranes to remove unincorporated material, followed by quantitation of incorporated labeled cholesterol by measuring the amount of radioactive, fluorescent, or other detectable label.

Figure 2:
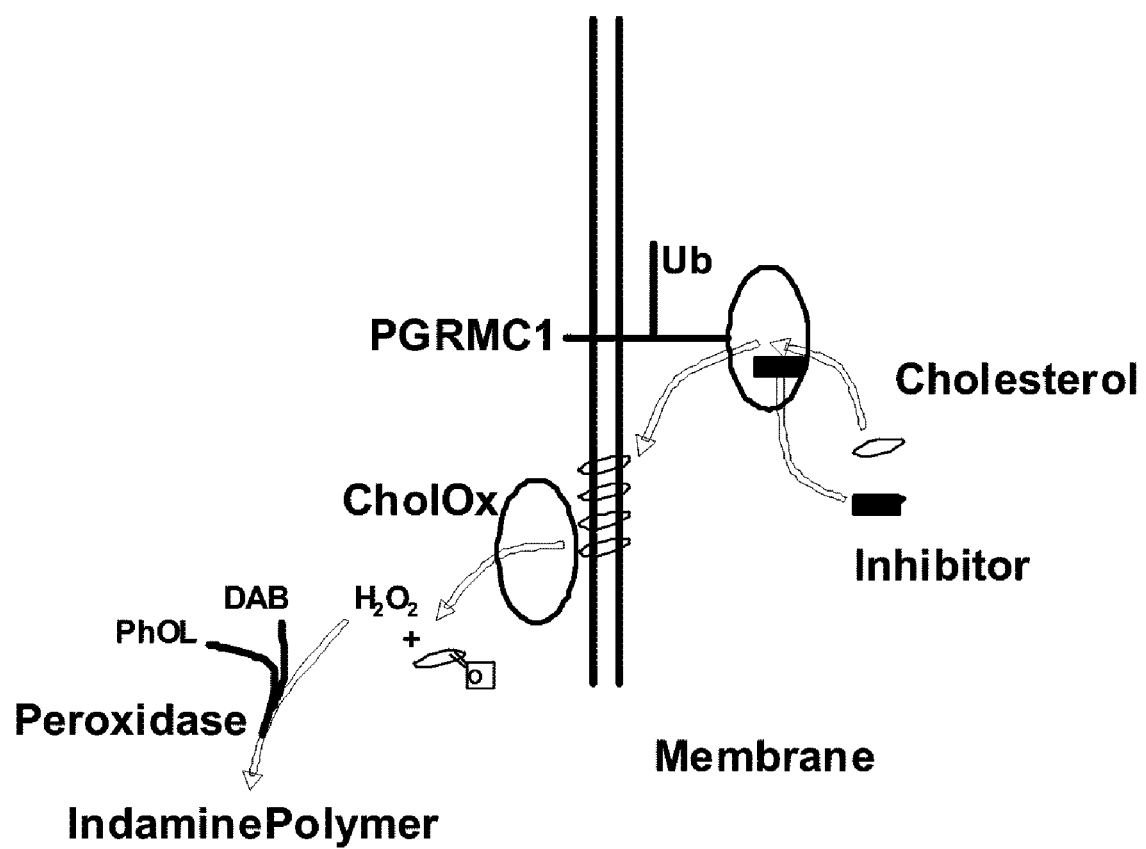
FIG. 2 illustrates an assay for determining the activity of PGRMC1 and related homologues based on the oxidation of cholesterol present in a membrane by the enzyme cholesterol oxidase.

In another embodiment, shown in FIG. 2, a calorimetric cholesterol oxidase assay is used to determine the amount of cholesterol incorporated into a membrane by PGRMC1 using the following materials: purified membranes containing PGRMC1, cholesterol, cholesterol oxidase, peroxidase, and DAB (3,3'-diaminobenzidine tetrahydrochloride) or other detection reagents for the detection of $H_2O_2$ produced by the activity of Cholesterol Oxidase.

Cholesterol preferentially associates with the lipid bilayer of the cell membrane and is actively or passively incorporated into the membrane by PGRMC1. Cholesterol Oxidase ("CO") is a water soluble enzyme that catalyzes the oxidation of cholesterol to cholest-4-en-3-one (cholestenone). The basic chemical reaction catalyzed by this enzyme is:

$$\text{Cholesterol} + O_2 \rightarrow H_2O_2 + \text{cholest-4-en-3-one}$$

It is known that CO physically associates with lipid bilayers without disrupting the cell membrane structure, which allows cholesterol to move directly from the membrane into the active site, without exposure to an aqueous solvent. The amount of $H_2O_2$ produced by CO in the above reaction is directly proportional to the amount of cholesterol substrate available in the membrane. The coupled step of the reaction, catalyzed by peroxidase, involves a reaction between $H_2O_2$ and DAB (3,3'-diaminobenzidine tetrahydrochloride) and production of a colored, luminescent, or fluorescent product which can be measured by the appropriate detection system. In other embodiments, the detection system may be the chemiluminescent substrate HyPerBlue (Lumigen, Inc.) or fluorescent detection systems for detection of $H_2O_2$ such as the QuantaBlu or FluoroCount systems (Pierce Chemical).

In a particular embodiment, this cholesterol oxidase assay can be characterized in three steps: Cholesterol incorporation; cholesterol oxidation and $H_2O_2$ evolvement; and detection. In an exemplary reaction, first, a 10 μL reaction containing 1 μl purified *E. coli* BL21 membrane containing recombinant PGRMC1 at a concentration of 0.01 mg/μL total protein, and 100 μM (or other desired concentration) cholesterol is incubated at 37° C. for a minimum of ten minutes. Then, 5 μL CO (0.5 U/μL) is added, and the reaction is again incubated at 37° C. for a minimum of ten minutes. Finally, a 65 μL solution containing 5 U peroxidase and 0.05% DAB (final concentration) is added to the reaction, mixed, well, and absorbance is read at 400 nM. Any other detection systems known in the art may also be used, and one skilled in the art will understand that reagent amounts and incubation times can be optimized as needed. Such detection systems form a detectable product that is, e.g., derived from or mediated by the detection reagent. It will be understood that various modifications of the above-described assay are included within the scope of the present invention.

According to multiple embodiments of the present invention, any assay that measures incorporation of sterol into membranes by PGRMC1 or a homologue can be used (i.e. assays using biological membranes or liposomes etc.) A variety of detection methods can also be used, such as colorimetric, barium detection, incorporation of a florescent analog, and the like.

This above-described cholesterol oxidase assay may be useful in screening for compounds that modulate the function of PGRMC1, which is useful because it can help to identify those compounds to treat disorders characterized by imbalanced cholesterol homeostasis, including increased levels of circulating LDL and coronary heart disease. Any compound may screened by the methods of the present invention.

Methods and Compositions for Modulating PGRMC1 Function

In another aspect, the present invention provides for a method of treating a patient with a disease characterized by defective cholesterol homeostasis mechanisms by administering a compound that affects the PGRMC1's ability to incorporate cholesterol into cell membranes, particularly MVB and ER membranes. In one aspect, inhibition of PGRMC1's ability to incorporate cholesterol into membranes by a small molecule or other agent may lead to sterol depletion of the endoplasmic reticulum. The homeostatic machinery in the endoplasmic reticulum would then be activated to increase expression of the cholesterol biosynthetic and LDL receptor uptake genes. Increased expression of the LDL receptor would lead to increased uptake of LDL and decreased circulating LDL.

Embodiments herein provide for the administration of compositions which modulate PGRMC1's ability to incorporate cholesterol into cell membranes to patients in a biologically compatible form suitable for pharmaceutical administration in vivo. Biologically compatible forms are active agents (i.e. pharmaceutical chemical, protein, gene, antibody, etc. of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result.

In one embodiment, the compound (e.g. a pharmaceutical chemical, protein, peptide, antibody, etc. of the embodiments) may be administered in a convenient manner such as subcutaneous, intravenous, by oral administration, inhalation, transdermal application, intravaginal application, topical application, intranasal or rectal administration. Depending on the route of administration, the active compound may be coated in a material to protect the compound from degradation by enzymes, acids and other natural conditions that may inactivate the compound.

A compound may be administered to a subject in an appropriate carrier or diluents, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

It will be apparent that, for any particular subject, specific dosage regimens may be adjusted over time according to the individual need. The preferred doses for administration can be anywhere in the range between about 0.01 mg and about 100 mg per ml of biologic fluid of treated patient. In one embodiment, the range can be between 1 and 100 mg/kg which can be administered daily, every other day, biweekly, monthly, etc. In another particular embodiment, the range can be between 10 and 75 mg/kg introduced weekly to a subject.

In another aspect, the present invention provides for compositions that have the ability to modulate PGRMC1's activity. In one embodiment, a number of planar hydrophobic compounds that directly bind to PGRMC1 can inhibit sterol delivery to the endoplasmic reticulum. In another embodiment, compounds lowering LDL cholesterol levels, such as niacin and the compounds found in red wine, likely bind PGRMC1 and inhibit its activity. Such compounds would essentially mimic the action of the statin drugs, which lower endoplasmic reticulum cholesterol levels by blocking cholesterol biosynthesis. However, statins, which inhibit HMG-CoA-reductase, a very early step in the pathway, also block the production of important metabolites such as ubiquinone, dolichol, and isoprenoids. The inability to synthesize these compounds likely causes some of the common side effects seen in statin-treated individuals. Inhibiting delivery of cholesterol to the endoplasmic reticulum provides an alternative to statin treatment without the unintended consequence of inhibiting the generation of side products. In an alternate embodiment, combination treatments may allow a reduction in statin dosage that would help relieve some of the side effects associated with current treatments.

Kits

In another aspect of the present invention, a kit or reagent system for practicing the described methods, including diagnosis and treatment, is provided. Such kits will contain a reagent combination including the particular elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and preferably including written instructions for the performance of assays. The kit may be adapted for any configuration of an assay and may include compositions for performing any of the various assay formats described herein.

EXAMPLES

The following examples are included to demonstrate illustrative embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials

The CHO cells (CHO-7) that were used in these studies are a previously described subline of CHO—K1 cells. Normal fibroblasts were provided by Dr. Raymond White (University of Utah) and NPC fibroblast cell lines were obtained from Coriell Laboratories (GM11095). Newborn calf lipoprotein-deficient serum (d>1.215 g/ml; cholesterol content of 33-61 µg/ml) and human LDL (d 1.019-1.063 g/ml) were prepared by ultracentrifugation. Lovastatin was provided by Alfred Alberts (Merck Sharp & Dohme, Rahway, N.J.). Yeast strains used for the synthetic genetic array (SGA) screen, which harbor specific gene knockouts, were obtained from the Research Genetics (Birmingham, Ala.) and were of the BY4741 genetic background. Plasmid vectors PCR2.1 and pcDNA3 were obtained from Invitrogen (Carlsbad, Calif.) and pET-16b from Novagen (Madison, Wis.). Plasmid IC52059, a construct containing a full length cDNA copy of PGRMC1, was obtained from the TIGR/ATTC consortium. The yeast PGMRC1 knockout was generated in a W303 background by homologous recombination using a PCR-generated cassette. Correct integration was confirmed by genomic PCR, and the knockout strain was backcrossed prior to use. Cholesterol was obtained from Alltech Chemicals. Progesterone was obtained from Sigma Chemical Company (St. Louis, Mo.). [1α, 2α(n)-$^3$H]Cholesterol (47 Ci/mmol) and [1,2,6,7,16,17-$^3$H]progesterone (109 Ci/mmol) were purchased from Amersham (Piscataway, N.J.). The anti-ubiquitin antibody, α-Ub, was provided by Martin Rechsteiner (University of Utah). Microarray slides containing 4609 human genes were obtained from the Huntsman Cancer Institute Microarray Facility at the University of Utah.

Microarray

Total RNA was isolated from fibroblast cell cultures using TRIzol Reagent (Gibco BRL, Carlsbad, Calif.) according to manufacturer's instructions. mRNA was isolated from total RNA using the Oligotex Isolation kit (Qiagen, Valencia, Calif.). The mRNA from the normal fibroblasts was labeled with Cy5-dCTP (red), and the mRNA from the NPC fibroblasts was labeled with Cy3-dCTP (green). These two probes were mixed and hybridized against target microarrays. A collection of 78 positive and negative control samples was included on each slide. These control samples included housekeeping genes, tissue-specific genes and non-human sequences. Fluorescent labeling efficiency and nonspecific cross hybridization were monitored using these controls. Images were captured on a Generation II Molecular Dynamics Microarray Scanner using red and green filter sets. Integrated spot intensities for each fluorescent channel were obtained using Molecular Dynamics ImageQuant software. Spot intensities were normalized to the total signal for all spots on the slide. Differences in expression were identified by comparing the mean intensities using a two-tailed T-test for unpaired samples assuming equal variances. Sixty-five genes demonstrated differences with P-value of 0.001 or less. Seven or eight of these genes would be expected to be false-positives based on random chance. Twenty genes demonstrated differences with a P-value of 0.00002 or less. False positive probability for these genes is less than 10%. These 20 genes were ranked based on fold difference.

Yeast Synthetic Genetic Array

A synthetic genetic array approach was performed essentially as described except that it was modified to be performed at high throughput using a robotic workstation, and image analysis and data capture were automated using custom software. Automation of the procedure provides a number of distinct advantages: (1) it reduces possible handling errors intrinsic to manual procedures; (2) it can be performed at high density thereby increasing throughput and the potential for replicates; and (3) control matings can be performed immediately adjacent to test matings, as opposed to on separate plates. The automated image analysis allows: (1) more accurate sample tracking; (2) tracking colony size and losses throughout the many steps of the procedure; (3) unbiased interpretation of the results; (4) the opportunity to create select composite images of the results; (5) the ability to hyperlink directly from the images and results to public databases; and (6) the ability to query the public databases for unusual patterns of gene function revealed by the results.

Briefly, each strain in the MATa haploid deletion collection (MATa his3Δ1 leu2Δ0 met15Δ0 ura3Δ0) was mated to the dap1Δ haploid query strain or ura3Δ control strain. Diploids were sporulated, and selections were used to generate a collection of colonies derived from spores that were MATa double mutants. Colony transfers were performed using a Biomek 2000 liquid handling robot with a floating pin tool. The screen was performed at a density of 1536 colony spots per ~3×5" plate (NUNC Omnitrays, Rochester, N.Y.) consisting of 384 mutant strains mated in duplicate to each of the ura3Δ control and the dap1Δ strains. Between transfers, the tool was sterilized by sonication for 20 s in 10% bleach, rinsed for 10 s in sterile water then 12 s in 100% ethanol, and dried over a fan for 30 seconds. Diploids were selected and sporulated followed by selection of MATa haploids, then MATa haploids containing the deletion collection allele, and finally MATa double mutants. Electronic images for each plate, at each step, were captured by scanning on a flatbed document scanner. Plate images were processed using the custom software which quantifies colony size based on differences in pixel intensity. This data was automatically entered into a relational database and queried to determine which colonies exhibited significant (>75%) colony size reduction on the ultimate (double mutant) selection plate as compared to previous plates. Colonies greatly reduced in size or absent only on the final plate were scored as indicating genetic interaction with the query strain, provided no colony size reduction was observed for the adjacent control strains (ura3Δ). This generated an unbiased list of genes that genetically interact with Dap1. The entire screen was then repeated allowing each strain in the knockout collection to be scored four times for genetic interaction with dap1Δ. Deletion strains where at least 3 of the 4 colonies were absent or reduced only on the final selection plate (double mutants), while at least 3 of the 4 adjacent controls (ura3Δ) were present and not reduced, were scored as genetically interacting with Dap1. This list was not biased by human intervention.

Ubiquitin Assay

A PCR-generated construct capable of expressing a flag epitope-tagged version of PGRMC1 (flag-PGRMC1) was made using vector IC52059 and primers JEM262 (5'-ATG AAT TCA TCA TGG ACT ACA AGG ACG ACG ATG ACA AGG CTG CTG CCG AGG ATG TGG TG-3' (SEQ ID NO: 8)) and JEM263 (5'-ATT CTA GAT TAA TCA TTT TTC CG-3' (SEQ ID NO: 9)). This construct was digested with EcoR1 and XbaI and ligated into pcDNA3. The subsequent pcDNA3:flag-PGRMC1 expression construct was and transfected into CHO cells using $CaPO_4$—mediated transfection, and pools of G418-resistant cells stably expressing flag-PGRMC1 were grown to confluence, harvested, homogenized, and fractionated. Protein concentrations were measured using the Bradford method and a 15 μg aliquot from each fraction was subjected to denaturing polyacrylamide gel electrophoresis (SDS-PAGE). The gel was transferred to a PDVF membrane, and incubated with mouse anti-flag or anti-ubiquitin antibody. Antibody binding was detected using anti-mouse HRP-conjugated secondary antibody and a peroxidase detection reaction (Immobilon Western: Millipore, Billerica, Mass.) according to the manufacturer's instructions. The membranes were exposed to film for 1 to 5 min using Kodak Clinic X-ray film.

Expression of $His_{10}$-PGRMC1 ($His_{10}$ disclosed as SEQ ID NO: 14) in Bacteria PCR reactions using primers pbp1n (5'-TGA TCT ACA TAT GGC GGC GGA AGA TGT GGT GGC GAC TG-3' (SEQ ID NO: 6)) and pbp2n (5'-CTG GAT CCT TAA TCA TTT TTC CGG GCA CTC-3' (SEQ ID NO: 7)) were performed on clone IC52094 to create a product containing the full length coding region of PGMRC1 flanked by Nde1 and BamHI restriction sites at the 5' and 3' ends, respectively. The PCR product was cloned directly into plasmid PCR2.1 using a T-A cloning kit (Invitrogen, Carlsbad, Calif.) in DH5-αcells. A clone (PCR2.1:PGRMC1) containing the correctly oriented insert was identified by restriction enzyme analysis. PCR2.1:PGRMC1 was then digested with Nde1 and BamHI and the fragment was directionally cloned into the Nde1/BamHI site of vector pET-16b in TOP10 F' cells (Invitrogen, Carlsbad, Calif.) to create plasmid pET-16b:PGRMC1, which encodes a 10×His (SEQ ID NO: 14) epitope tag at the $NH_2$ terminus of PGRMC1.

For bacterial expression, BL21 (DE3) cells (Stratagene, LaJolla, Calif.) were transformed with pET-16b:PGRMC1 and plated on LB agar plates containing ampicillin (amp). One to 7 days later, individual colonies were harvested and used to inoculate small volume (5-200 mL) liquid cultures of LB-amp media. Cultures were grown with shaking at 37° C. until early log phase ($OD_{600}$=0.6). IPTG was added to a final concentration of 0.5M and the cultures were incubated for another 4 hours at 37° C. or overnight at room temperature. $His_{10}$-PGRMC1 ($His_{10}$ disclosed as SEQ ID NO: 14) expression was confirmed by SDS-PAGE followed by Coomassie stain and western blot using mouse monoclonal anti-tetra-His (SEQ ID NO: 15) antibody (Qiagen, Valencia, Calif.).

Membrane Preparation

IPTG-induced cells were harvested by centrifugation (5,000 rpm; 5 min) and washed with ice-cold $H_2O$. The pellet was resuspended in 5 mL buffer A (50 mM Tris-HCl pH 7.5, 150 mM NaCl, 0.1% NP40, and 10% glycerol) with 5-10 mg lysozyme, and incubated on ice for 30 min. The cells were then disrupted by three bursts of sonication (45 sec) at high intensity with a 45 sec cooling period between bursts. Soluble material was removed by centrifugation (15,000 rpm, 10 min) and the pellet resuspended in 5 mL buffer A. $His_{10}$-PGRMC1 ($His_{10}$ disclosed as SEQ ID NO: 14) was confirmed to be present in purified membranes by SDS-PAGE followed by Coomassie stain and western blot using anti-tetra-His (SEQ ID NO: 15) antibody (Qiagen). Total protein in the $His_{10}$-PGRMC1 ($His_{10}$ disclosed as SEQ ID NO: 14) transformed and untransformed purified membranes was determined by the Bradford method and membranes were normalized to 10 μg/μL total protein (diluted with buffer A). Purified membranes were then aliquoted and stored frozen until use.

PGRMC1 Binding Assay

The standard 10 μL binding reaction contained 10 μp purified membranes (total protein) and 10 μM [$^3$H] progesterone or [$^3$H] cholesterol (3,000-5,000 cpm) in buffer A: 20% ethanol. Stock solutions (100 μM) of [$^3$H] cholesterol and [$^3$H] progesterone containing ~4×10$^4$ cpm/μL, were prepared in 95% ethanol. Reactions were prepared in clear 2.0 mL microcentrifuge tubes on ice. To start the reaction, the microfuge tube was briefly mixed (vortex) and placed at 37° C. Following a 10 to 30 min incubation, the tubes were centrifuged in a microfuge (~13,000 rpm) for 2 min. The supernatant was carefully removed and the pellet was washed with an additional 10 μL water. After a second round of centrifugation (2 min; 13,000 rpm), the resulting supernatant was combined with the first and the pellet was resuspended in 20 μL $H_2O$, Scintillation fluid (700 μL Wallac Optiflour) was added to each fraction and the fractions were mixed extensively. The fractions were then counted in a multi-well scintillation counter (Wallac Microbeta Triluxmax, Waltham, Mass.) for 30 seconds each. Binding are reported as μ/moles of ligand bound per mg of membrane protein. $His_{10}$-PGRMC1 ($His_{10}$ disclosed as SEQ ID NO: 14)-specific binding is reported as the difference in binding between transformed and untransformed bacteria. Experimental deviations from the standard assay conditions are noted in individual figure legends. Parametric analyses of the saturation data using models assuming 1, 2 and 3 binding sites revealed a single binding site in membranes prepared from untransformed bacteria and 2 or 3 binding sites in membranes prepared from PGRMC1 transformed bacteria. The 2 binding site model was chosen as most parsimonious since the 3 binding site model did not provide a statistically better fit.

Example 1

PGRMC1 is Up-Regulated in NPC Fibroblasts

Figure 3:
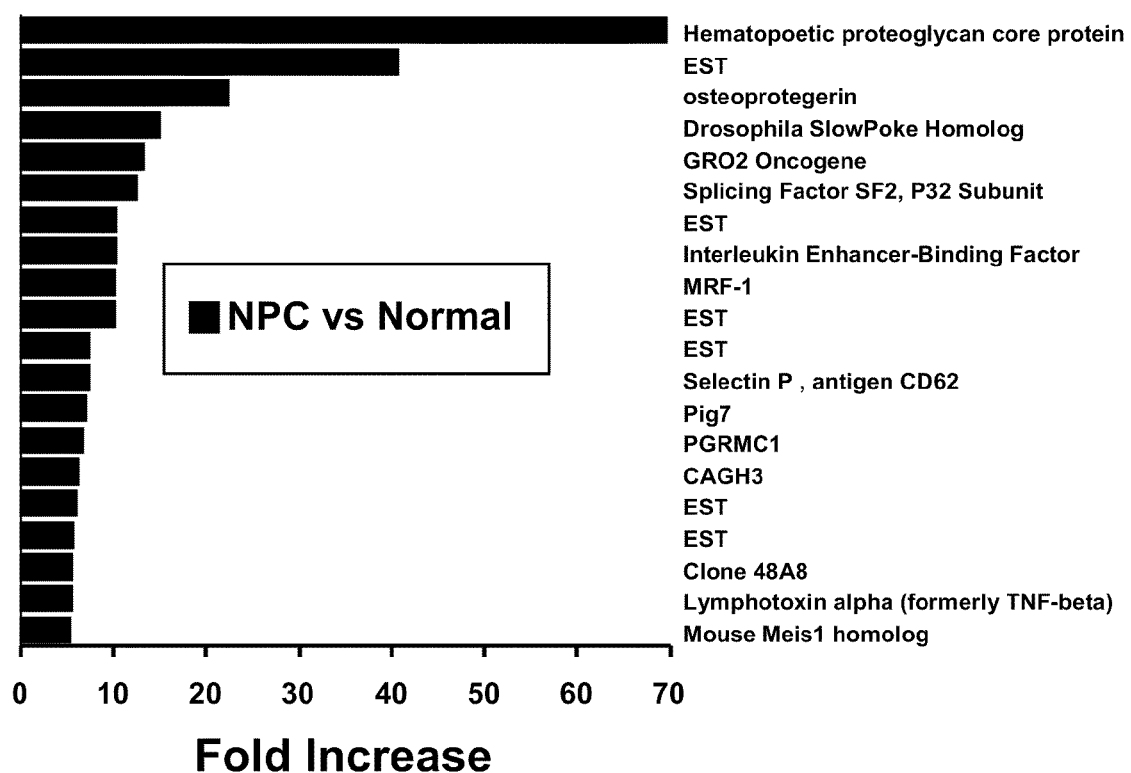
FIG. 3 illustrates abnormal gene expression in NPC1 mutant fibroblasts according to an embodiment of the present invention. mRNA was isolated from normal and NPC1 mutant fibroblasts treated to maximize NPC1 function and subjected to microarray analysis as described. Shown are the 20 genes that appeared to have a significant difference in expression levels between the two cells (p-values<0.00002).

To determine the effects that mutant NPC1 has on global gene expression, a gene expression microarray analysis was performed between normal and NPC1 mutant fibroblasts. In order to maximize NPC1 function, cells were treated with lovistatin and LDL prior to mRNA preparation. First strand cDNA from wild-type fibroblasts was labeled with Cy5-dCTP (red), and cDNA from NPC1 mutant fibroblasts was labeled with Cy3-dCTP (green). The probes were mixed and hybridized against 4609 target PCR products arrayed onto glass slides in duplicate. Of the 4609 genes, twenty genes, shown in FIG. 3, demonstrated the highest fold difference, ranging from 5-fold to 70-fold. Each difference was significant having p-values of less than 0.00002. One gene in particular, the putative progesterone binding protein PGRMC1 (p-value 0.0000009), showed a 6-fold higher expression in NPC1 mutant fibroblasts versus normal fibroblasts. Since progesterone is known to block intracellular sterol transport and has been proposed to phenocopy the NPC1 mutant phenotype, it is possible that PGRMC1 plays a role in the same endocytic pathway as NPC1. The increased PGRMC1 expression may be an attempt by the cell to compensate for the transport defect and/or the accumulation of cholesterol caused by the NPC1 mutation. Additionally, there are several sterol biosynthetic phenotypes associated with PGRMC1 in yeast and humans making PGRMC1 an attractive target for further study of intracellular sterol transport.

Example 2

DAP1 Genetically Interacts with Genes in the ESCRT1 Pathway

PGRMC1 and its homologues have been implicated to be involved in a number of distinct biological processes. In *S. cerevisiae* and *S. pombe*, the PGRMC1 homologue Dap1 mutant exhibits a decreased steady state ergosterol level with a corresponding increase in ergosterol precursors. Additionally, dap1Δ *S. cerevisiae* appears to be resistant to the polyene antibiotic amphotericin B at 37° C. (data not shown). Amphotericin B functions in a similar manner as nystatin in binding to and depleting membrane ergosterol thereby killing the cell.

A Synthetic Genetic Array Screen was performed to further explore which biological processes and pathways in which Dap1 is involved. This technique consists of mating a dap1Δ query or ura3 Δ control strain to nearly 5,000 yeast deletion strains lacking a single non-essential gene. The resulting diploids are sporulated and subjected to a series of selections to generate a double mutant collection, which is then scored for fitness defects. Synthetic lethality or sickness in the double mutants indicates a genetic interaction between the two genes. To eliminate human error as much as possible screens were automated to a Biomek 2000 liquid handling system with a floating pin replicator. The screen was performed in duplicate at a density of 1536 individual colony spots per selection plate, representing two ura3Δ control and two dap1Δ query strains mated to 384 different library mutants. To eliminate bias in interpretation, software was developed to automatically qualify colony presence/absence and quantify relative size based on pixel intensity of digital images of each selection plate. This information was fed into a relational database and queried to determine which dap1Δ::: xxxΔ (xxx=any non-essential yeast gene) colonies were absent or greatly reduced in size on the final selection plate compared to the previous plates with little or no reduction in size of the corresponding ura3Δ::xxxΔ control colonies. dap1Δ::xxxΔ colonies meeting these criteria were automatically scored as gene xxx genetically interacting with Dap1.

Out of 4728 total genes in the mutant library, 3988 were assayed at least twice in our screens with 108 of those genetically interacting with Dap1. Twenty-six were linked to the DAP1 locus and dismissed, leaving 82 unlinked interactors. A search of the public databases revealed 241 Gene Ontology (GO) annotations associated with these 82 genes. The probability of generating these specific GO annotations in a random sampling of a similar number of all possible GO annotations was then calculated. GO annotations and the genes associated with them that were hit multiple times with a very low p-value were categorized as highly significant. Genes hit multiple times with a moderate p-value were categorized as moderately significant. GO annotations and associated genes hit only once (no p-value) but having high chi-square values were also significant. These lists were then examined for genes relevant to this study. Apparent were highly significant genes involved in intracellular transport and membrane targeting and most interestingly members of the ESCRT1 complex (Table 1). The ESCRT1 complex is well known in yeast and mammalian cells to recognize and target mono-ubiquitinated proteins to the multi-vesicular body (MVB) pathway for degradation or recycling. Since the MVB is a sterol rich organelle, it is probable that PGRMC1 is targeted to the MVB where it performs its biological function.

TABLE 1

Synthetic Genetic Interactions with dap1Δ.

|  | Observed | Expected | ChiSquare | P value |
|---|---|---|---|---|
| High Significance GO Term | | | | |
| GARP complex | 3 | 0.1 | 84.10 | 5.47E−19 |
| ESCRT1 complex | 2 | 0.12 | 29.45 | 5.73E−08 |
| Fatty acid biosynthesis | 3 | 0.12 | 69.12 | 9.79E−16 |
| Moderate Significance GO Term | | | | |
| Protein targeting to membrane | 2 | 0.22 | 14.40 | 1.48E−04 |
| Late endosome to vacuole transport | 2 | 0.47 | 4.98 | 2.56E−02 |
| Significant GO Term | | | | |
| Extrinsic to endoplasmic reticulum membrane | 1 | 0.02 | 48.02 | N/A |
| Acetate biosynthesis | 1 | 0.04 | 23.04 | |

Example 3

PRGMC1 is Mono-Ubiquitinated

Figure 4:
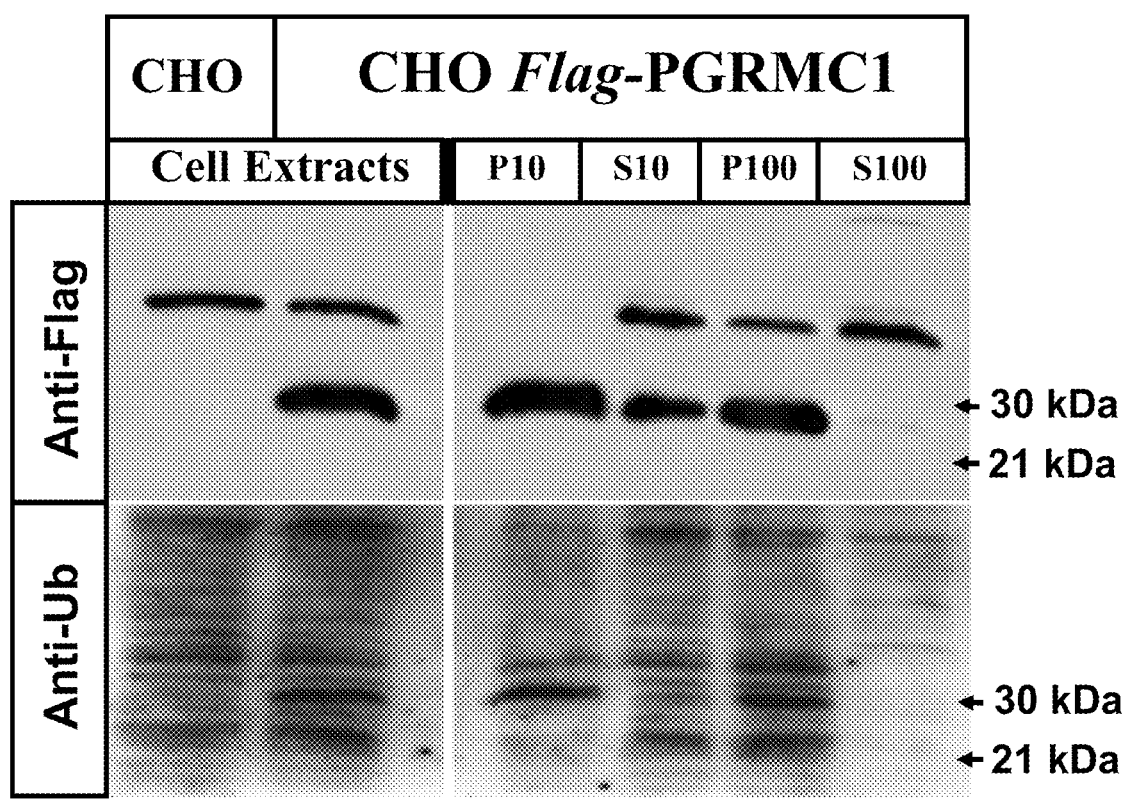
FIG. 4 illustrates sub-cellular distribution and ubiquitination of flag-PGRMC1 according to an embodiment of the present invention. Uppermost bands represent what appears to be a soluble protein cross reaction with the anti-flag antibody.

PRGMC1 has a predicted molecular weight of 21 kDa. Without exception, studies of PGRMC1 in various tissues have detected it as a predominately membrane-associated ~28 kDa and ~56 kDa protein. To further explore this apparent discrepancy in molecular weight and examine sub-cellular localization, differential centrifugation with ±flag-PGRMC1 transfected CHO cells was performed. CHO cells stably expressing flag-PGRMC1 were fractionated, centrifuged, and separated into the pellet (P) and supernatant (S) fractions of 10,000 and 100,000×g spins respectively. Fifteen (15) μg of each fraction was subjected to SDS-PAGE and probed with anti-flag antibody. PGRMC1 was observed to be membrane-associated and migrating as an approximate 30 kDa protein (FIG. 4, top). This difference between expected and observed molecular weight suggests a post-translational modification. Ubiquitin is an excellent candidate to be this modification having a molecular weight of approximately 8.5 kDa. To test this hypothesis, the sub-cellular localization blot with an anti-ubiquitin antibody was probed. The anti-ubiquitin antibody recognized a variety of different proteins in both untransfected (FIG. 4, bottom; lane 1) and transfected (lane 2) cells. Transfected cells, however, showed an additional protein of approximately 30 kDa that comigrated with flag-PGRMC1 and was found mainly in the P10 and P100 fractions.

Example 4

Binding of Cholesterol to PGRMC1

In order to better understand PGRMC1's biological function and to study ligand binding, an in vitro binding assay was developed. *E. coli* BL21 codon plus (RIPL) cells were transformed with a vector encoding PGRMC1 that was epitope tagged with 10 histidine (SEQ ID NO: 14) residues at the NH$_2$-terminus. Untransformed BL21 cells were used as the control. A purification procedure was performed to remove soluble proteins and cell components from the transformed (+PGRMC1) and untransformed (−PGRMC1) bacterial membranes. The resulting purified membranes were confirmed for the presence and absence of His$_{10}$-PGRMC1 (His$_{10}$ disclosed as SEQ ID NO: 14) respectively by Coomassie stain and western blot using anti-His antibody. The membranes with [$^3$H] progesterone or [$^3$H] cholesterol were then incubated. The membranes were spun out, washed, and counted in a scintillation counter. His$_{10}$-PGRMC1 (His$_{10}$ disclosed as SEQ ID NO: 14) specific binding was then determined by subtracting total membrane-associated ligand (nmols/mg protein) in membranes prepared from untransformed bacteria (−PGRMC1) with membranes purified from bacteria expressing His$_{10}$-PGRMC1 (His$_{10}$ disclosed as SEQ ID NO: 14) (+PGRMC1).

Figure 5:
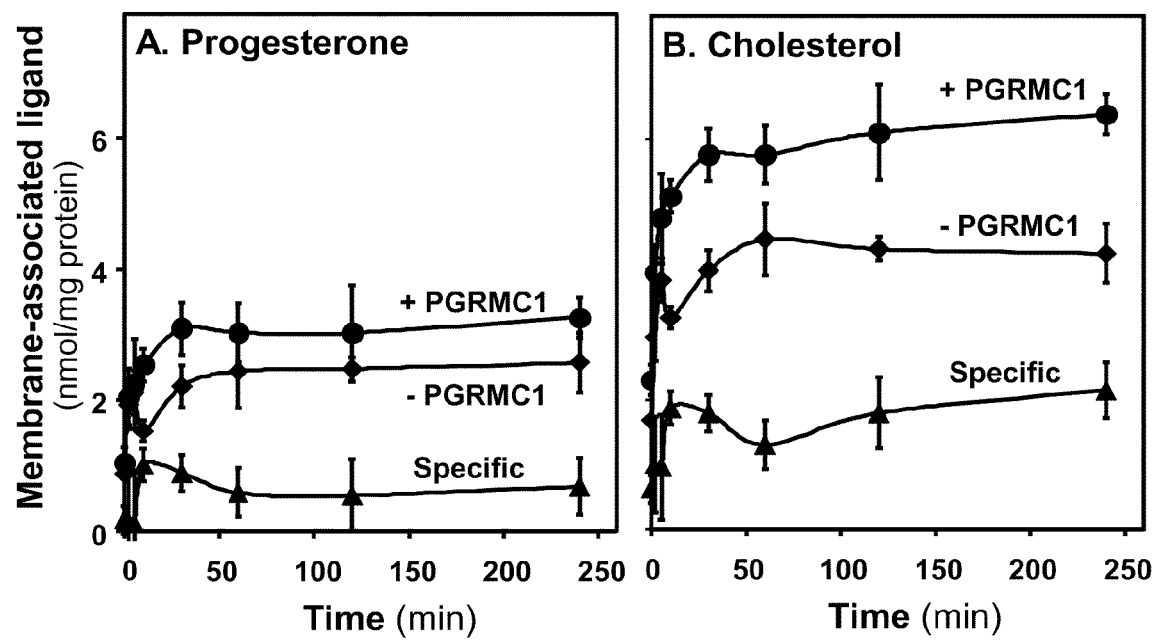
FIG. 5 illustrates time course of cholesterol (B) and progesterone (A) binding to $His_{10}$-PGRMC1 ($His_{10}$ disclosed as SEQ ID NO: 14) according to an embodiment of the present invention. Each data point is the average of triplicate assays. Error bars represent one standard deviation.
Figure 6:
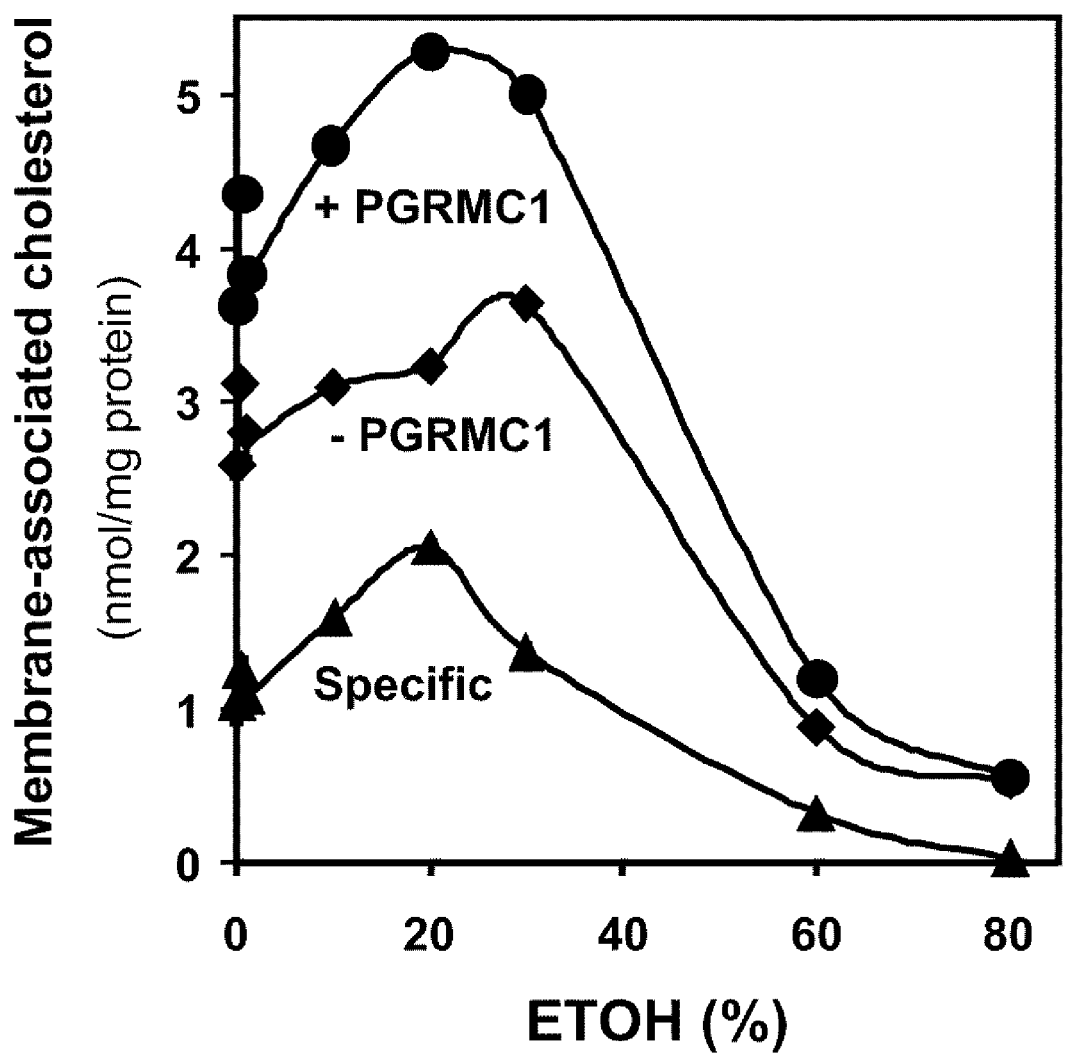
FIG. 6 illustrates cholesterol binding to $His_{10}$-PGRMC1 ($His_{10}$ disclosed as SEQ ID NO: 14) under varying ethanol concentrations according to an embodiment of the present invention. Each data point is the average of duplicate assays. Error bars represent one standard deviation.

PGRMC1 was initially identified based on its ability to bind progesterone. To validate the in vitro assay, the ability of His$_{10}$-PGRMC1 (His$_{10}$ disclosed as SEQ ID NO: 14) to bind progesterone over time was tested. [$^3$H] progesterone was incubated with purified membranes for the indicated times. The reactions were then processed and ligand binding quantified as described. Non-specific progesterone binding in membranes −PGRMC1 and increased binding in membranes +PGRMC1 was observed due to specific binding of progesterone to His$_{10}$-PGRMC1 (His$_{10}$ disclosed as SEQ ID NO: 14) (FIG. 5A). Binding occurred rapidly and reached a saturation/equilibrium of approximately 0.5 nmoles progesterone bound per mg protein within 15-30 minutes. These results suggest that the in vitro assay is valid for examining His$_{10}$-PGRMC1 (His$_{10}$ disclosed as SEQ ID NO: 14) ligand binding. To test the hypothesis that PGRMC1's natural ligand is likely to be a sterol, a time course of cholesterol binding was performed. As shown in FIG. 5B, there was an increase in both non-specific cholesterol binding in membranes −PGRMC1 and specific binding in membranes +PGRMC1. Cholesterol binding to His$_{10}$-PGRMC1 (His$_{10}$ disclosed as SEQ ID NO: 14) occurred and reached saturation/equilibrium at approximately the same rate as progesterone but cholesterol binding was universally 2-3 fold higher at every time point (~2 nmoles/mg protein). Binding of both ligands was temperature dependent as very little His$_{10}$-PGRMC1 (His$_{10}$ disclosed as SEQ ID NO: 14) specific binding occurred at temperatures below 15° C. Because cholesterol is relatively insoluble in aqueous solutions, the ethanol concentration in the reactions was varied to maximize specific binding of cholesterol to His$_{10}$-PGRMC1 (His$_{10}$ disclosed as SEQ ID NO: 14) in the assay. Although specific binding in the absence of ethanol was observed, it was found that binding was most efficient at 20% ethanol and decreased rapidly at higher concentrations (FIG. 6). Subsequent reactions were all performed with 20% ethanol final concentration.

Figure 7:
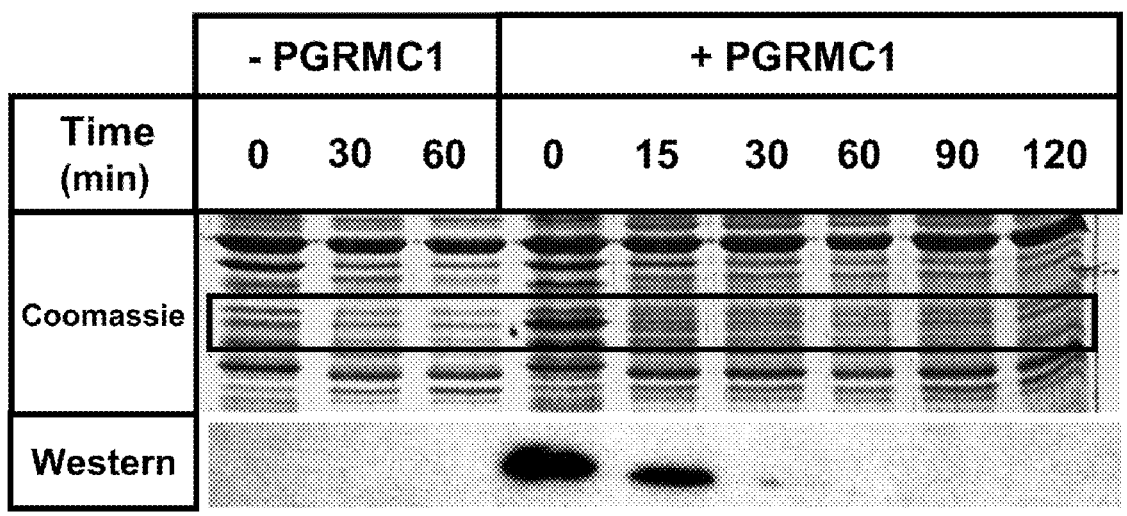
FIG. 7 illustrates trypsin proteolysis of membranes ±$His_{10}$-PGRMC1 ($His_{10}$ disclosed as SEQ ID NO: 14) according to an embodiment of the present invention.

To ensure that binding of progesterone and cholesterol was due to His$_{10}$-PGRMC1 (His$_{10}$ disclosed as SEQ ID NO: 14) and not a non-specific interaction, the membranes were proteolyzed prior to ligand binding. PGRMC1 has multiple lysine and arginine residues, especially in the ligand binding domain, which render it particularly susceptible to trypsin degradation. Trypsin rapidly degraded His$_{10}$-PGRMC1 (His$_{10}$ disclosed as SEQ ID NO: 14) with no detectable protein by western blot within 60 min (FIG. 7). The protease-treated membranes, now essentially devoid of His10-PGRMC1 (His$_{10}$ disclosed as SEQ ID NO: 14), were used in the in vitro binding assay. Incubating [$^3$H] progesterone and [$^3$H] cholesterol with proteolyzed membranes resulted in a complete loss (Table 2) of His$_{10}$-PGRMC1 (His$_{10}$ disclosed as SEQ ID NO: 14) specific binding to both ligands while non-treated membranes exhibited His$_{10}$-PGRMC1 (His$_{10}$ disclosed as SEQ ID NO: 14) specific binding as previously observed.

TABLE 2

Binding of [$^3$H] Cholesterol and Progesterone to protease-treated His$_{10}$-PGRMC1 (His$_{10}$ disclosed as SEQ ID NO: 14).

| | Membrane-Associated [$^3$H] Ligand | | | |
| | Progesterone | | Cholesterol | |
| Treatment Protease | − | + | − | + |
| | nmoles/mg protein | | | |
| −PGRMC1 | 2.4 ± 0.1 | 1.6 ± 0.2 | 3.7 ± 0.3 | 2.6 ± 0.2 |
| +PGRMC1 | 3.1 ± 0.3 | 1.6 ± 0.3 | 5.2 ± 0.3 | 2.6 ± 0.2 |
| Specific | 0.7 ± 0.2 | 0.0 ± 0.1 | 1.5 ± 0.2 | 0.0 ± 0.2 |

Figure 8:
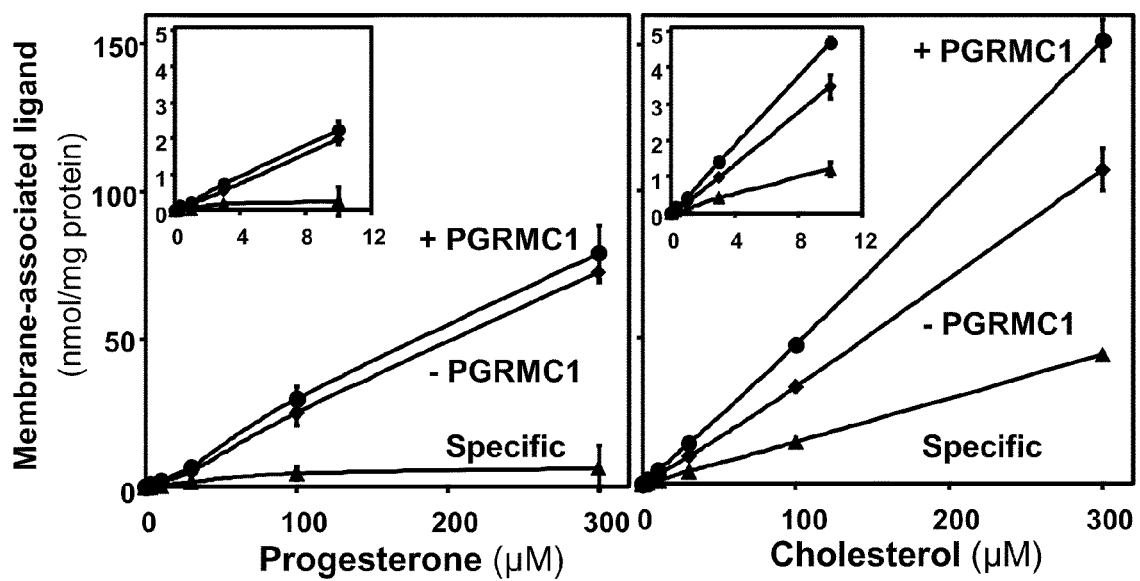
FIG. 8 illustrates saturation binding of progesterone and cholesterol to $His_{10}$-PGRMC1 ($His_{10}$ disclosed as SEQ ID NO: 14) according to an embodiment of the present invention. Saturation of progesterone (left) and cholesterol (right) to $His_{10}$-PGRMC1 ($His_{10}$ disclosed as SEQ ID NO: 14). Each data point is the average of triplicate assays. Error bars represent one standard deviation.

Next, the question of whether binding of ligand to His$_{10}$-PGRMC1 (His$_{10}$ disclosed as SEQ ID NO: 14) is saturable was examined. FIG. 8 shows the saturation curves for binding of [$^3$H] progesterone and [$^3$H] cholesterol to His$_{10}$-PGRMC1 (His$_{10}$ disclosed as SEQ ID NO: 14). Ligand binding time was held constant while increasing the ligand concentration by half logs in each experiment. The ligand concentration spanned four orders of magnitude from lowest to highest. Under these conditions, the specific binding of progesterone to His$_{10}$-PGRMC1 (His$_{10}$ disclosed as SEQ ID NO: 14) appeared to be saturable and reached half-maximal at approximately 50 µM (FIG. 8A). Interestingly, specific binding of cholesterol to His$_{10}$-PGRMC1 (His$_{10}$ disclosed as SEQ ID NO: 14) did not appear to be saturable under these conditions, and cholesterol binding steadily increased over the entire range of ligand concentrations (FIG. 8B). Cholesterol was only partially soluble in our assay at concentrations greater than 3 mM so testing saturation at higher concentrations was unable to be performed. These results suggest that both progesterone and cholesterol bind to His$_{10}$-PGRMC1 (His$_{10}$ disclosed as SEQ ID NO: 14), and the increased binding observed with cholesterol is due to a greater number of cholesterol binding sites; so many more that even at high cholesterol concentrations binding is not saturated. These data seem useful because, as previously indicated, a study of conserved motifs within PGRMC1 reveals a single, presumably monomeric, ligand binding domain.

To further explore the nature of ligand binding to His$_{10}$-PGRMC1 (His$_{10}$ disclosed as SEQ ID NO: 14), several in silico modeling experiments fitting the saturation data to different models of ligand binding were performed. The best statistical fit of the data was to a two binding site model. The first category of binding sites, present in both membranes expressing $His_{10}$-PGRMC1 ($His_{10}$ disclosed as SEQ ID NO: 14) (+PGRMC1) and not expressing $His_{10}$-PGRMC1 ($His_{10}$ disclosed as SEQ ID NO: 14) (−PGRMC1) represents non-specific ligand association with the membranes. Non-specific binding occurs for both cholesterol and progesterone with an approximate $K_d$ of 1 mM and $8-9 \times 10^9$ binding sites per reaction (Table 3). The second category of binding site, present only in membranes expressing $His_{10}$-PGRMC1 ($His_{10}$ disclosed as SEQ ID NO: 14) (+PGRMC1), represents specific binding. With progesterone, this specific binding occurs with a $K_d$ of 5.5 nM and approximately 20,000 binding sites. Cholesterol binds with a 15-fold lower $K_d$ (0.35 nM) to approximately 80,000 binding sites (Table 3). The question then naturally arises as to the nature of these binding sites, whether they are all protein associated, and whether they represent separate sites on the same protein.

TABLE 3

PGRMC1 Saturation Data Fit to a Two Binding Site Model.

|  | Progesterone | | Cholesterol | | |
| --- | --- | --- | --- | --- | --- |
|  | −PGRMC1 | +PGRMC1 | −PGRMC1 | +PGRMC1 | |
| $K_d 1$ | 1.7 | 1.0 | 0.9 | 1.0 | mM |
| Q1 | $8.4 \times 10^9$ | $8.0 \times 10^9$ | $8.4 \times 10^9$ | $9.6 \times 10^9$ | Sites |
| $K_d 2$ | 0 | 5.54 | 0 | 0.35 | nM |
| Q2 | 0 | 19,260 | 0 | 81,709 | Sites |

Figure 9:
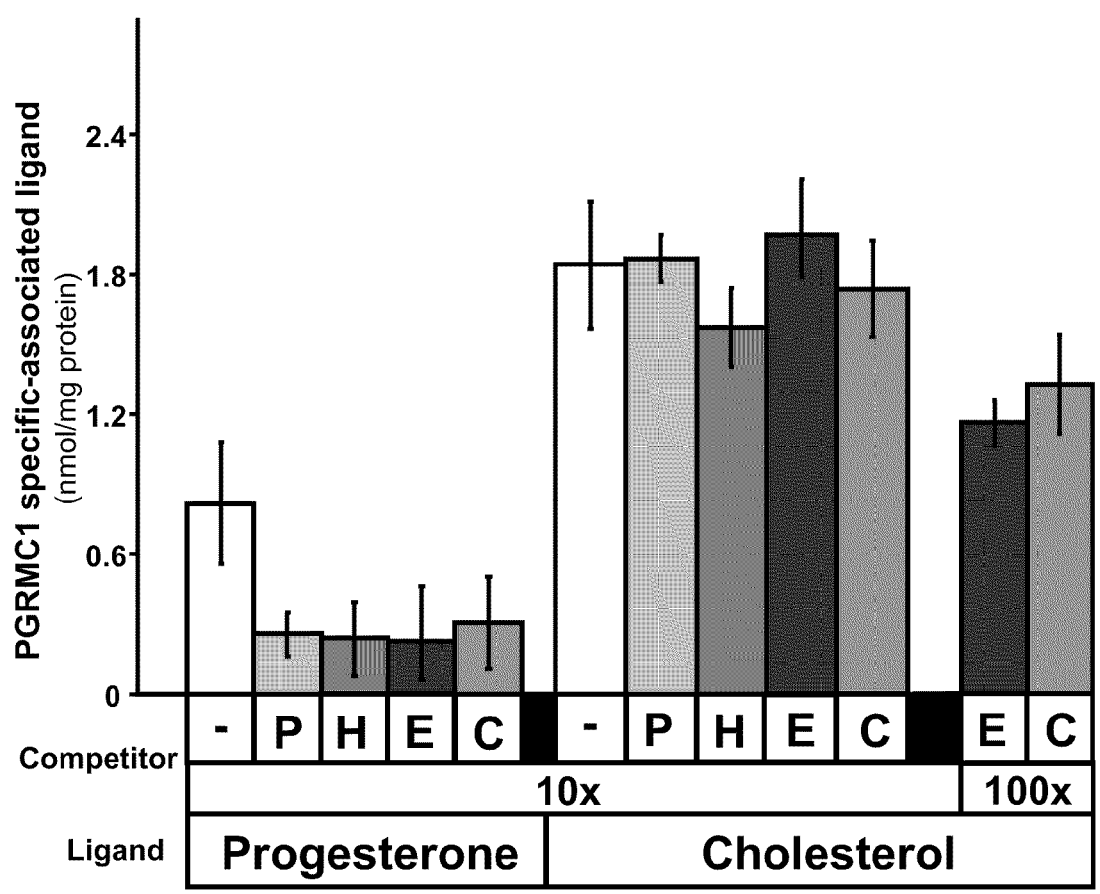
FIG. 9 illustrates competition between [$^3$H] progesterone and cholesterol and cold progesterone (P), Heme (H), Ergosterol (E), and Cholesterol (C) for $His_{10}$-PGRMC1 ($His_{10}$ disclosed as SEQ ID NO: 14) binding according to an embodiment of the present invention. Data represent the average of triplicate assays; error bars represent one standard deviation.

To test whether progesterone and cholesterol compete for the same specific binding site, the direct binding of [$^3$H] progesterone or [$^3$H] cholesterol to $His_{10}$-PGRMC1 ($His_{10}$ disclosed as SEQ ID NO: 14) in the presence of various cold competitors was examined. In these experiments, the standard amount of [$^3$H] ligand was combined with a cold competitor at either 10 or 100-fold higher concentration and mixed well to ensure homogeneity. These stock ligand solutions were then used in the standard binding assay as described. It was observed that, under these conditions, specific binding of [$^3$H] progesterone to $His_{10}$-PGRMC1 ($His_{10}$ disclosed as SEQ ID NO: 14) was greatly reduced by the presence of excess cholesterol indicating that cholesterol competes with progesterone for the same binding site (FIG. 9, progesterone, lane C).

The ability of other putative ligands reported in the literature to compete with progesterone binding was examined. These experiments revealed that both heme (H) and ergosterol (E) in ten-fold excess amounts also reduced specific [$^3$H] progesterone binding $His_{10}$-PGRMC1 ($His_{10}$ disclosed as SEQ ID NO: 14). As a control, cold progesterone (P) was used as a competitor and it was observed that excess cold progesterone competes with [$^3$H] progesterone for $His_{10}$-PGRMC1 ($His_{10}$ disclosed as SEQ ID NO: 14) binding. Contrastingly, binding of [$^3$H] cholesterol to $His_{10}$-PGRMC1 ($His_{10}$ disclosed as SEQ ID NO: 14) was unaffected by the presence of progesterone, ergosterol, or heme at ten-fold higher concentrations (FIG. 9, cholesterol). It was not until competitor concentrations were 100-fold higher than ligand that a reduction of cholesterol binding was observed. Interestingly, unlike a ten-fold excess cold progesterone for [$^3$H] progesterone, a ten-fold excess cold cholesterol did not begin to reduce specific [$^3$H] cholesterol binding until the cold cholesterol amount was 100-fold greater than [$^3$H] cholesterol.

Figure 10:
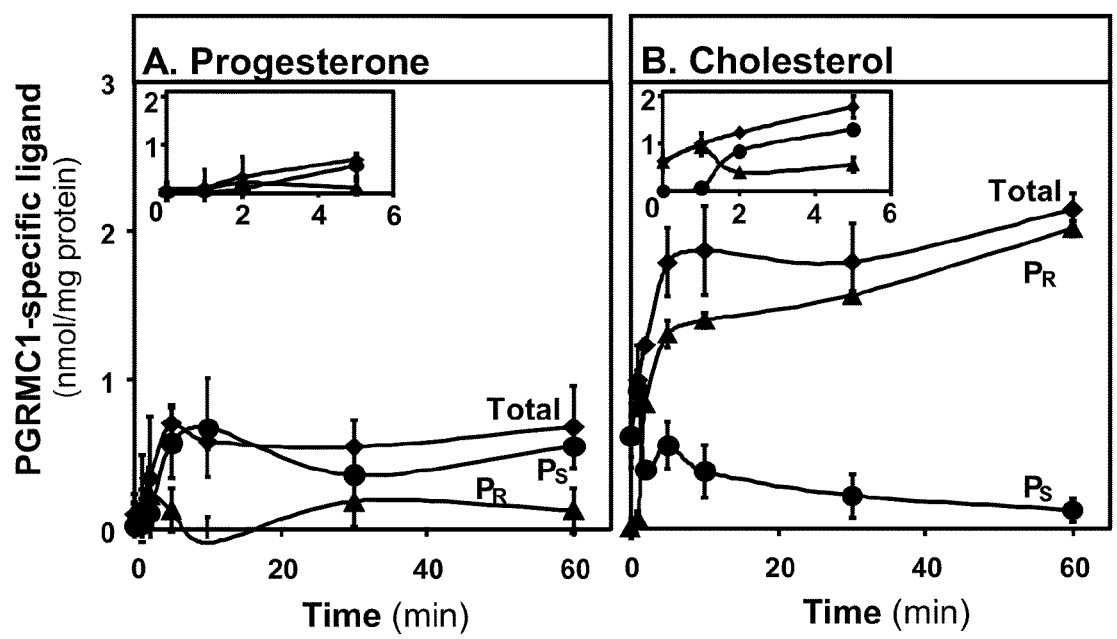
FIG. 10 illustrates binding of progesterone (A) and cholesterol (B) to membranes ±$His_{10}$-PGRMC1 ($His_{10}$ disclosed as SEQ ID NO: 14) according to an embodiment of the present invention. Curves illustrate total (Total, diamonds; membrane+protein) ligand binding, protease sensitive ($P^S$, circles; protein) binding, and protease resistant ($P^R$, triangles; membrane) binding. Data represent the average of triplicate assays; error bars represent one standard deviation.

Since data from the competition assays indicate that progesterone and cholesterol bind to the same site within $His_{10}$-PGRMC1 ($His_{10}$ disclosed as SEQ ID NO: 14), the reason for the observation of more cholesterol binding in our assays was examined. There appear to be two plausible explanations: one possibility is that there are more cholesterol-specific binding sites on $His_{10}$-PGRMC1 ($His_{10}$ disclosed as SEQ ID NO: 14) that comprise the increase in observed binding; the other is that $His_{10}$-PGRMC1 ($His_{10}$ disclosed as SEQ ID NO: 14) is catalyzing the incorporation of cholesterol into the membrane. To distinguish between these possibilities, a coupled time-course proteolysis experiment was performed. In these studies, [$^3$H] progesterone and [$^3$H] cholesterol were incubated with membranes ±$His_{10}$-PGRMC1 ($His_{10}$ disclosed as SEQ ID NO: 14) for increasing time periods. At the end of the incubation period, the membranes were isolated, washed, and resuspended in a trypsin solution to remove all $His_{10}$-PGRMC1 ($His_{10}$ disclosed as SEQ ID NO: 14) protein. In this manner any ligand specifically bound to $His_{10}$-PGRMC1 ($His_{10}$ disclosed as SEQ ID NO: 14) would be protease-sensitive and be removed from the membrane fraction. Any ligand incorporated into the membrane or other protected site will be protease-resistant and remain in the membrane fraction. After proteolysis the reactions were separated by centrifugation into protease-resistant (membrane) and protease-sensitive (supernatant) fractions and ligand amount determined. This data was then graphed as seen in FIG. 10 as total specific binding (Total, diamonds), specific binding that was protease-sensitive ($P_S$, circles), and specific binding that was protease-resistant ($P_R$, triangles). Total specific binding of progesterone (FIG. 10A, diamonds) increasing over time and occurring at levels consistent with previous studies was observed. It was found that essentially all specific progesterone binding was protease-sensitive, (FIG. 10A, circles) indicating it was mainly protein-associated with virtually no protease-resistant or membrane-associated binding component (FIG. 10A, triangles). Similarly, total cholesterol binding (FIG. 10B, diamonds) over time with kinetics and at levels consistent with previous studies was observed but it was also found that, as reaction time lengthened, the cholesterol ligand was increasingly protease-resistant and membrane-associated (FIG. 10B, triangles). This corresponded with a protease-sensitive, protein-associated binding component that started out high (FIG. 10B), essentially equal to protease-sensitive progesterone binding at early time points, and decreased over time as more ligand became associated with the membrane (FIG. 10B, circles). These results indicate that the increased cholesterol binding in membranes +$His_{10}$-PGRMC1 ($His_{10}$ disclosed as SEQ ID NO: 14) results from the transfer or incorporation of cholesterol from PGRMC1 to the membrane or membrane-associated binding site and not a greater number of binding sites within $His_{10}$-PGRMC1 ($His_{10}$ disclosed as SEQ ID NO: 14) itself. It is important to note that this ligand incorporation reaction is specific to bound cholesterol as it was observed that all bound progesterone was protein associated. Collectively our findings describe an important and previously uncharacterized function for PGRMC1 and sterol binding proteins in general, that of catalyzing the incorporation of cholesterol into membranes.

Equivalents

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

We claim:

1. A method of screening for compounds that modulate the activity of PGRMC1 or a homologue thereof comprising:
   (a) contacting a test compound with cholesterol and a membrane-bound PGRMC1 or a homologue thereof to form a reaction mixture; and
   (b) determining whether incorporation of cholesterol into the membrane is increased or decreased in the presence of the test compound, wherein a decrease in the incorporation is an indication that the test compound inhibits the activity of PGRMC1 or homologue thereof, and an increase in the incorporation is an indication that the test compound enhances the activity of PGRMC1, wherein the PGRMC1 or homologue thereof is selected from the group consisting of SEQ ID NO: 1 or a protein having an amino acid sequence that is at least 95% identical to SEQ ID NO: 1, SEQ ID NO: 2 or a protein having an amino acid sequence that is at least 95% identical to SEQ ID NO: 2, SEQ ID NO: 3 or a protein having an amino acid sequence that is at least 95% identical to SEQ ID NO: 3, SEQ ID NO: 4 or a protein having an amino acid sequence that is at least 95% identical to SEQ ID NO: 4, and SEQ ID NO: 5 or a protein having an amino acid sequence that is at least 95% identical to SEQ ID NO: 5.

2. The method of claim 1, wherein the PGRMC1 or homologue thereof is SEQ ID NO: 1 or a protein having an amino acid sequence that is at least 95% identical to SEQ ID NO: 1.

3. The method of claim 1, wherein the PGRMC1 or homologue thereof is SEQ ID NO: 1.

4. The method of claim 1, wherein the step of determining whether incorporation of cholesterol into the membrane is increased or decreased in the presence of the test compound comprises:
   (a) contacting the reaction mixture with cholesterol oxidase;
   (b) adding peroxidase and a detection reagent; and
   (c) measuring the formation of a detectable product.

5. The method of claim 4, wherein the detectable product is a colored, luminescent or fluorescent product.

6. The method of claim 4, wherein the detection reagent is 3,3'-diaminobenzidine tetrahydrochloride.

7. The method of claim 1, wherein the membrane-bound PGRMC1 protein or homologue thereof is produced recombinantly.

8. The method of claim 1, wherein the membrane-bound PGRMC1 protein or homologue thereof is produced in *E. coli*.

9. The method of claim 1, wherein the test compound is contacted with cholesterol and a membrane-bound PGRMC1 or a homologue thereof under physiological conditions.

10. The method of claim 1, wherein the method of screening identifies compounds that inhibit incorporation of cholesterol into a membrane.

11. A method of screening compounds that modulate the activity of PGRMC1 or a homologue thereof comprising:
    (a) providing a solution comprising (i) membranes associated with PGRMC1 or a homologue thereof; (ii) cholesterol; and (iii) a test compound;
    (b) incubating the solution under physiological conditions;
    (c) contacting the solution with cholesterol oxidase;
    (d) adding peroxidase and a detection reagent to produce a detectable product; and
    (e) measuring the production of the detectable product to determine whether incorporation of cholesterol into the membrane is increased or decreased in the presence of the test compound, wherein the PGRMC1 or homologue thereof is selected from the group consisting of SEQ ID NO: 1 or a protein having an amino acid sequence that is at least 95% identical to SEQ ID NO: 1, SEQ ID NO: 2 or a protein having an amino acid sequence that is at least 95% identical to SEQ ID NO: 2, SEQ ID NO: 3 or a protein having an amino acid sequence that is at least 95% identical to SEQ ID NO: 3, SEQ ID NO: 4 or a protein having an amino acid sequence that is at least 95% identical to SEQ ID NO: 4, and SEQ ID NO: 5 or a protein having an amino acid sequence that is at least 95% identical to SEQ ID NO: 5.

12. The method of claim 11, wherein a decrease in the incorporation is an indication that the test compound inhibits the activity of PGRMC1 or homologue thereof, and an increase in the incorporation is an indication that the test compound enhances the activity of PGRMC1.

13. The method of claim 11, wherein the detectable product is a colored, luminescent or fluorescent product.

14. The method of claim 11, wherein the detection reagent is 3,3'-diaminobenzidine tetrahydrochloride.

15. The method of claim 11, wherein the PGRMC1 protein or homologue thereof is produced recombinantly.

16. The method of claim 11, wherein the PGRMC1 protein or homologue thereof is produced in *E. coli*.

17. The method of claim 1, wherein the PGRMC1 or homologue thereof is SEQ ID NO: 5 or a protein having an amino acid sequence that is at least 95% identical to SEQ ID NO: 5.

* * * * *

SEQUENCE LISTING

```
<160> NUMBER OF SEQ ID NOS: 15

<210> SEQ ID NO 1
<211> LENGTH: 195
<212> TYPE: PRT
<213> ORGANISM: Homo sapiens

<400> SEQUENCE: 1

Met Ala Ala Glu Asp Val Val Ala Thr Gly Ala Asp Pro Ser Asp Leu
1               5                   10                  15

Glu Ser Gly Gly Leu Leu His Glu Ile Phe Thr Ser Pro Leu Asn Leu
            20                  25                  30

Leu Leu Leu Gly Leu Cys Ile Phe Leu Leu Tyr Lys Ile Val Arg Gly
        35                  40                  45

Asp Gln Pro Ala Ala Ser Gly Asp Ser Asp Asp Glu Pro Pro Pro
    50                  55                  60

Leu Pro Arg Leu Lys Arg Arg Asp Phe Thr Pro Ala Glu Leu Arg Arg
65                  70                  75                  80

Phe Asp Gly Val Gln Asp Pro Arg Ile Leu Met Ala Ile Asn Gly Lys
                85                  90                  95

Val Phe Asp Val Thr Lys Gly Arg Lys Phe Tyr Gly Pro Glu Gly Pro
                100                 105                 110

Tyr Gly Val Phe Ala Gly Arg Asp Ala Ser Arg Gly Leu Ala Thr Phe
            115                 120                 125

Cys Leu Asp Lys Glu Ala Leu Lys Asp Glu Tyr Asp Asp Leu Ser Asp
        130                 135                 140

Leu Thr Ala Ala Gln Gln Glu Thr Leu Ser Asp Trp Glu Ser Gln Phe
145                 150                 155                 160

Thr Phe Lys Tyr His His Val Gly Lys Leu Leu Lys Glu Gly Glu Glu
                165                 170                 175

Pro Thr Val Tyr Ser Asp Glu Glu Pro Lys Asp Glu Ser Ala Arg
            180                 185                 190

Lys Asn Asp
        195

<210> SEQ ID NO 2
<211> LENGTH: 195
<212> TYPE: PRT
```

```
<213> ORGANISM: Mus musculus

<400> SEQUENCE: 2

Met Ala Glu Asp Val Val Ala Thr Gly Ala Asp Pro Ser Glu Leu
1               5                   10                  15

Glu Gly Gly Gly Leu Leu His Glu Ile Phe Thr Ser Pro Leu Asn Leu
            20                  25                  30

Leu Leu Leu Gly Leu Cys Ile Phe Leu Leu Tyr Lys Ile Val Arg Gly
            35                  40                  45

Asp Gln Pro Gly Ala Ser Gly Asp Asn Asp Asp Glu Pro Pro
    50                  55                  60

Leu Pro Arg Leu Lys Arg Arg Asp Phe Thr Pro Ala Glu Leu Arg Arg
65                  70                  75                  80

Phe Asp Gly Val Gln Asp Pro Arg Ile Leu Met Ala Ile Asn Gly Lys
                85                  90                  95

Val Phe Asp Val Thr Lys Gly Arg Lys Phe Tyr Gly Pro Glu Gly Pro
                100                 105                 110

Tyr Gly Val Phe Ala Gly Arg Asp Ala Ser Arg Gly Leu Ala Thr Phe
            115                 120                 125

Cys Leu Asp Lys Glu Ala Leu Lys Asp Glu Tyr Asp Asp Leu Ser Asp
            130                 135                 140

Leu Thr Pro Ala Gln Gln Glu Thr Leu Ser Asp Trp Asp Ser Gln Phe
145                 150                 155                 160

Thr Phe Lys Tyr His His Val Gly Lys Leu Leu Lys Glu Gly Glu Glu
                165                 170                 175

Pro Thr Val Tyr Ser Asp Asp Glu Glu Pro Lys Asp Glu Thr Ala Arg
                180                 185                 190

Lys Asn Glu
        195

<210> SEQ ID NO 3
<211> LENGTH: 223
<212> TYPE: PRT
<213> ORGANISM: Rattus norvegicus

<400> SEQUENCE: 3

Met Ala Glu Asp Val Val Ala Thr Gly Ala Asp Pro Ser Glu Leu
1               5                   10                  15

Glu Gly Gly Gly Leu Leu Gln Glu Ile Phe Thr Ser Pro Leu Asn Leu
            20                  25                  30

Leu Leu Leu Gly Leu Cys Ile Phe Leu Leu Tyr Lys Ile Val Arg Gly
            35                  40                  45

Asp Gln Pro Gly Ala Ser Gly Asp Asn Asp Asp Glu Pro Pro
    50                  55                  60

Leu Pro Arg Leu Lys Pro Arg Asp Phe Thr Pro Ala Glu Leu Arg Arg
65                  70                  75                  80

Tyr Asp Gly Val Gln Asp Pro Arg Ile Leu Met Ala Ile Asn Gly Lys
                85                  90                  95

Val Phe Asp Val Thr Lys Gly Arg Lys Phe Tyr Gly Pro Glu Gly Pro
                100                 105                 110

Tyr Gly Val Phe Ala Gly Arg Asp Ala Ser Arg Gly Leu Ala Thr Phe
            115                 120                 125

Cys Leu Asp Lys Glu Ala Leu Lys Asp Glu Tyr Asp Asp Leu Ser Asp
            130                 135                 140

Leu Thr Pro Ala Gln Gln Glu Thr Leu Asn Asp Trp Asp Ser Gln Phe
145                 150                 155                 160
```

```
Ser Ser Pro Ser Ser Thr Ile Thr Trp Gly Lys Leu Leu Glu Gly Ala
            165                 170                 175

Glu Glu Pro Ile Val Tyr Ser Asp Asp Glu Glu Gln Lys Met Arg Leu
            180                 185                 190

Leu Gly Arg Val Thr Glu Ala Val Ser Gly Ala Tyr Leu Phe Leu Tyr
        195                 200                 205

Phe Ala Lys Ser Phe Val Thr Phe Gln Ser Val Phe Thr Thr Trp
    210                 215                 220
```

<210> SEQ ID NO 4
<211> LENGTH: 223
<212> TYPE: PRT
<213> ORGANISM: Homo sapiens

<400> SEQUENCE: 4

```
Met Ala Ala Gly Asp Gly Asp Val Lys Leu Gly Thr Leu Gly Ser Gly
1               5                   10                  15

Ser Glu Ser Ser Asn Asp Gly Gly Ser Glu Ser Pro Gly Asp Ala Gly
            20                  25                  30

Ala Ala Ala Glu Gly Gly Gly Trp Ala Ala Ala Leu Ala Leu Leu
            35                  40                  45

Thr Gly Gly Gly Glu Met Leu Leu Asn Val Ala Leu Val Ala Leu Val
        50                  55                  60

Leu Leu Gly Ala Tyr Arg Leu Trp Val Arg Trp Gly Arg Arg Gly Leu
65                  70                  75                  80

Gly Ala Gly Ala Gly Ala Gly Glu Glu Ser Pro Ala Thr Ser Leu Pro
                85                  90                  95

Arg Met Lys Lys Arg Asp Phe Ser Leu Glu Gln Leu Arg Gln Tyr Asp
            100                 105                 110

Gly Ser Arg Asn Pro Arg Ile Leu Leu Ala Val Asn Gly Lys Val Phe
            115                 120                 125

Asp Val Thr Lys Gly Ser Lys Phe Tyr Gly Pro Ala Gly Pro Tyr Gly
        130                 135                 140

Ile Phe Ala Gly Arg Asp Ala Ser Arg Gly Leu Ala Thr Phe Cys Leu
145                 150                 155                 160

Asp Lys Asp Ala Leu Arg Asp Glu Tyr Asp Asp Leu Ser Asp Leu Asn
                165                 170                 175

Ala Val Gln Met Glu Ser Val Arg Glu Trp Glu Met Gln Phe Lys Glu
            180                 185                 190

Lys Tyr Asp Tyr Val Gly Arg Leu Leu Lys Pro Gly Glu Glu Pro Ser
            195                 200                 205

Glu Tyr Thr Asp Glu Glu Asp Thr Lys Asp His Asn Lys Gln Asp
        210                 215                 220
```

<210> SEQ ID NO 5
<211> LENGTH: 172
<212> TYPE: PRT
<213> ORGANISM: Homo sapiens

<400> SEQUENCE: 5

```
Met Val Gly Pro Ala Pro Arg Arg Leu Arg Pro Leu Ala Ala Leu
1               5                   10                  15

Ala Leu Val Leu Ala Leu Ala Pro Gly Leu Pro Thr Ala Arg Ala Gly
            20                  25                  30

Gln Thr Pro Arg Pro Ala Glu Arg Gly Pro Val Arg Leu Phe Thr
            35                  40                  45
```

```
Glu Glu Glu Leu Ala Arg Tyr Gly Gly Glu Glu Asp Gln Pro Ile
         50                  55                  60

Tyr Leu Ala Val Lys Gly Val Val Phe Asp Val Thr Ser Gly Lys Glu
 65                  70                  75                  80

Phe Tyr Gly Arg Gly Ala Pro Tyr Asn Ala Leu Thr Gly Lys Asp Ser
                 85                  90                  95

Thr Arg Gly Val Ala Lys Met Ser Leu Asp Pro Ala Asp Leu Thr His
            100                 105                 110

Asp Thr Thr Gly Leu Thr Ala Lys Glu Leu Glu Ala Leu Asp Glu Val
        115                 120                 125

Phe Thr Lys Val Tyr Lys Ala Lys Tyr Pro Ile Val Gly Tyr Thr Ala
    130                 135                 140

Arg Arg Ile Leu Asn Glu Asp Gly Ser Pro Asn Leu Asp Phe Lys Pro
145                 150                 155                 160

Glu Asp Gln Pro His Phe Asp Ile Lys Asp Glu Phe
                165                 170
```

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tgatctacat atggcggcgg aagatgtggt ggcgactg                            38

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ctggatcctt aatcattttt ccgggcactc                                     30

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
atgaattcat catggactac aaggacgacg atgacaaggc tgctgccgag gatgtggtg    59

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
attctagatt aatcattttt ccg                                            23

<210> SEQ ID NO 10
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 10

Ala Thr Asn Tyr
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Lys Lys Ala Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Lys Asp Asn
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Asp Glu Phe
1

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 14

His His His His His His His His His His
1               5                   10

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      4xHis tag

<400> SEQUENCE: 15

His His His His
1
```